US009192660B2

(12) United States Patent
Weiner et al.

(10) Patent No.: US 9,192,660 B2
(45) Date of Patent: Nov. 24, 2015

(54) INFLUENZA NUCLEIC ACID MOLECULES AND VACCINES MADE THEREFROM

(71) Applicant: The Trustees of the University of Pennsylvania, Philadelphia, PA (US)

(72) Inventors: David B Weiner, Merion, PA (US); Matthew P Morrow, Bala Cynwyd, PA (US); Jian Yan, Havertown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/661,808

(22) Filed: Oct. 26, 2012

(65) Prior Publication Data

US 2013/0052222 A1 Feb. 28, 2013

Related U.S. Application Data

(62) Division of application No. 12/694,238, filed on Jan. 26, 2010, now Pat. No. 8,298,820.

(51) Int. Cl.

| | |
|---|---|
| ***A61K 39/145*** | (2006.01) |
| ***A61K 31/7088*** | (2006.01) |
| ***A61K 45/06*** | (2006.01) |
| ***A61K 39/12*** | (2006.01) |
| *A61K 39/00* | (2006.01) |

(52) U.S. Cl.

CPC ........... *A61K 39/145* (2013.01); *A61K 31/7088* (2013.01); *A61K 39/12* (2013.01); *A61K 45/06* (2013.01); *A61K 2039/53* (2013.01); *A61K 2039/54* (2013.01); *C12N 2760/16134* (2013.01)

(58) Field of Classification Search

CPC ............ A61K 39/145; A61K 2039/53; A61K 31/7088; A61K 39/12

USPC .......................................................... 424/209

See application file for complete search history.

(56) References Cited

U.S. PATENT DOCUMENTS

| | | | |
|---|---|---|---|
| 4,510,245 | A | 4/1985 | Cousens et al. |
| 4,554,101 | A | 11/1985 | Hopp |
| 4,722,848 | A | 2/1988 | Paoletti et al. |
| 4,790,987 | A | 12/1988 | Compans et al. |
| 4,797,368 | A | 1/1989 | Carter et al. |
| 4,920,209 | A | 4/1990 | Davis et al. |
| 4,945,050 | A | 7/1990 | Sanford et al. |
| 5,017,487 | A | 5/1991 | Stunnenberg et al. |
| 5,036,006 | A | 7/1991 | Sanford et al. |
| 5,077,044 | A | 12/1991 | Stocker |
| 5,110,587 | A | 5/1992 | Paoletti et al. |
| 5,112,749 | A | 5/1992 | Brey, III et al. |
| 5,174,993 | A | 12/1992 | Paoletti |
| 5,223,424 | A | 6/1993 | Cochran et al. |
| 5,225,336 | A | 7/1993 | Paoletti |
| 5,240,703 | A | 8/1993 | Cochran |
| 5,242,829 | A | 9/1993 | Panicali et al. |
| 5,273,525 | A | 12/1993 | Hofmann |
| 5,294,441 | A | 3/1994 | Curtiss, III |
| 5,294,548 | A | 3/1994 | McLinden et al. |
| 5,310,668 | A | 5/1994 | Ellis et al. |
| 5,387,744 | A | 2/1995 | Curtiss, III |
| 5,389,368 | A | 2/1995 | Curtiss, III |
| 5,424,065 | A | 6/1995 | Curtiss, III et al. |
| 5,451,499 | A | 9/1995 | Cochran |
| 5,453,364 | A | 9/1995 | Paoletti |
| 5,462,734 | A | 10/1995 | Letchworth et al. |
| 5,470,734 | A | 11/1995 | Sondermeijer et al. |
| 5,474,935 | A | 12/1995 | Chatterjee et al. |
| 5,482,713 | A | 1/1996 | Paoletti |
| 5,580,859 | A | 12/1996 | Felgner et al. |
| 5,591,439 | A | 1/1997 | Plotkin et al. |
| 5,593,972 | A | 1/1997 | Weiner et al. |
| 5,643,579 | A | 7/1997 | Hung et al. |
| 5,650,309 | A | 7/1997 | Wong-Staal et al. |
| 5,676,594 | A | 10/1997 | Joosten |
| 5,698,202 | A | 12/1997 | Ertl et al. |
| 5,703,055 | A | 12/1997 | Felgner et al. |
| 5,739,118 | A | 4/1998 | Carrano et al. |
| 5,817,637 | A | 10/1998 | Weiner et al. |
| 5,830,876 | A | 11/1998 | Weiner et al. |
| 5,955,088 | A | 9/1999 | Ghiasi et al. |
| 5,962,428 | A | 10/1999 | Carrano et al. |
| 5,981,505 | A | 11/1999 | Weiner et al. |
| 6,034,298 | A | 3/2000 | Lam et al. |
| 6,042,836 | A | 3/2000 | Berman et al. |
| 6,110,161 | A | 8/2000 | Mathiesen |
| 6,156,319 | A | 12/2000 | Cohen et al. |

(Continued)

FOREIGN PATENT DOCUMENTS

| | | |
|---|---|---|
| WO | WO 9324640 | 12/1993 |
| WO | WO 9416737 | 4/1994 |

(Continued)

OTHER PUBLICATIONS

Genebank Accession No. GQ323564.
Genebank Accession No. GQ323560.
Genebank Accession No. FJ966952.
Genebank Accession No. FJ966082.
Genebank Accession No. GQ255897.
Genebank Accession No. CY041645.
Genebank Accession No. CY041637.
Genebank Accession No. CY041629.
Genebank Accession No. GQ261272.

(Continued)

*Primary Examiner* — Zachariah Lucas
*Assistant Examiner* — Barry A Chestnut
(74) *Attorney, Agent, or Firm* — Riverside Law LLP

(57) ABSTRACT

Provided herein are nucleic acid sequences that encode novel consensus amino acid sequences of HA hemagglutinin, as well as genetic constructs/vectors and vaccines expressing the sequences. Also provided herein are methods for generating an immune response against one or more Influenza A serotypes using the vaccines that are provided.

19 Claims, 5 Drawing Sheets

(56) References Cited

U.S. PATENT DOCUMENTS

| | | | |
|---|---|---|---|
| 6,261,281 | B1 | 7/2001 | Mathiesen et al. |
| 6,589,529 | B1 | 7/2003 | Choi et al. |
| 6,697,669 | B2 | 2/2004 | Dev et al. |
| 6,733,994 | B2 | 5/2004 | Weiner |
| 6,939,862 | B2 | 9/2005 | Bureau et al. |
| 6,958,060 | B2 | 10/2005 | Mathiesen et al. |
| 7,238,522 | B2 | 7/2007 | Hebel et al. |
| 7,245,963 | B2 | 7/2007 | Draghia-Akli et al. |
| 7,328,064 | B2 | 2/2008 | Mathiesen et al. |
| 7,459,162 | B2 | 12/2008 | Yang et al. |
| 7,527,800 | B2 | 5/2009 | Yang et al. |
| 7,566,458 | B2 | 7/2009 | Yang et al. |
| 2004/0175727 | A1 | 9/2004 | Draghia-Akli et al. |
| 2005/0042229 | A1 | 2/2005 | Yang et al. |
| 2005/0052630 | A1 | 3/2005 | Smith et al. |
| 2006/0217338 | A1 | 9/2006 | Lu et al. |
| 2007/0105193 | A1 | 5/2007 | Vilalta et al. |
| 2007/0286873 | A1 | 12/2007 | Williams |
| 2008/0091135 | A1 | 4/2008 | Draghia-Akli |
| 2008/0299151 | A1* | 12/2008 | Fomsgaard ................ 424/206.1 |
| 2009/0169505 | A1 | 7/2009 | Draghia-Akli et al. |
| 2009/0208531 | A1 | 8/2009 | Nabel |
| 2010/0166787 | A1 | 7/2010 | Weiner |

FOREIGN PATENT DOCUMENTS

| | | | |
|---|---|---|---|
| WO | WO2009026397 | | 2/2009 |
| WO | WO2010060430 | * | 6/2010 |

OTHER PUBLICATIONS

Genebank Accession No. GQ323446.
Genebank Accession No. CY041597.
Genebank Accession No. CY041589.
Genebank Accession No. CY041581.
Genebank Accession No. CY040653.
Genebank Accession No. CY041573.
Genebank Accession No. CY041565.
Genebank Accession No. CY041541.
Genebank Accession No. GQ258462.
Genebank Accession No. CY039527.
Genebank Accession No. CY041557.
Genebank Accession No. CY041549.
Genebank Accession No. GQ283484.
Genebank Accession No. GQ283493.
Genebank Accession No. GQ303340.
Genebank Accession No. FJ966959.
Genebank Accession No. GQ287619.
Genebank Accession No. GQ267839.
Genebank Accession No. GQ268003.
Genebank Accession No. CY041621.
Genebank Accession No. CY041613.
Genebank Accession No. CY041605.
Genebank Accession No. DQ868374.
Genebank Accession No. GQ483315.
Genebank Accession No. DQ868375.
Genebank Accession No. GQ323579.
Genebank Accession No. GQ323576.
Genebank Accession No. GQ323574.
Genebank Accession No. GQ323551.
Genebank Accession No. GQ323530.
Genebank Accession No. GQ323520.
Genebank Accession No. GQ323509.
Genebank Accession No. GQ323495.
Genebank Accession No. GQ323489.
GenebankAccession No. GQ323486.
Genebank Accession No. GQ323483.
Genebank Accession No. GQ323464.
Genebank Accession No. GQ323455.
Genebank Accession No. GQ323451.
Genebank Accession No. GQ323443.
Genebank Accession No. GQ293077.
Genebank Accession No. GQ288372.
Genebank Accession No. GQ290059.
Genebank Accession No. GQ287625.
Genebank Accession No. GQ287627.
Genebank Accession No. GQ287623.
Genebank Accession No. GQ287621.
Genebank Accession No. GQ286175.
GenebankAccession No. GQ283488.
Genebank Accession No. GQ280797.
Genebank Accession No. GQ280264.
Genebank Accession No. GQ280121.
Genebank Accession No. GQ259909.
Genebank Accession No. GQ261277.
Genebank Accession No. GQ253498.
Genebank Accession No. GQ323473.
Genebank Accession No. GQ323470.
Genebank Accession No. GQ253492.
Genebank Accession No. FJ998208.
Genebank Accession No. FJ982430.
Genebank Accession No. FJ981615.
Genebank Accession No. FJ981613.
Genebank Accession No. FJ981612.
Genebank Accession No. FJ971076.
Genebank Accession No. FJ969540.
Genebank Accession No. FJ969511.
Genebank Accession No. FJ969509.
Genebank Accession No. FJ966982.
Genebank Accession No. GQ255900.
Genebank Accession No. GQ255901.
Genebank Accession No. FJ966974.
Genebank Accession No. GQ261275.
Genebank Accession No. FJ966960.
Garten, R.J. et al., "Antigenic and Genetic Characteristics of Swine-Origin 2009 A (H1N1) Influenza Viruses Circulating in Humans", Science, 2009, 325:197-201.
Laddy, D.J. et al., "Immunogenicity of novel consensus-based DNA vaccines against avian influenza", Vaccine, 2007, 25:2984-2989.
Chen, M.W. et al., "A consensus hemagglutinin based DNA vaccine that protects mice against divergent H5N1 influenza viruses", PNAS USA, 2008, 105(36)13538-13543.
Laddy, D.J. et al., "Heterosubtypic protection against pathogenic human . . . electroporation of synthetic consensus DNA antigens", PLoS One, 2008, 3(6):e2517.
Li, X. et al., "Protection against respiratory syncytial virus infection by DNA immunization", J. Exp. Med., 1998, 188:681-688.
Deml. L. et al., "Multiple effects of codon usage optimization of expression and immunogenicity of DNA candidate . . . virus type 1 gag protein", J. Viral., 2001, 75:10991-11001.
Chattergoon, M. et al., "Genetic immunization: a new era in vaccines and immune therapeutics", FASEB J, 1997, 11(10):753-763.
Liu, M.A. and Ulmer, J.B., "Human clinical trials of plasmid DNA vaccines", Adv Genet, 2005, 55:25-40.
Andre, S. et al., "Increased immune response elicited by DNA vaccination with a synthetic gp 120 sequence with optimized codon usage", J Virol, 1998, 72(2):1497-1503.
Frelin, L. et al., "Codon optimization and mRNA amplification effectively enhances . . . hepatitis C virus nonstructural 3/4A gene", Gene Ther, 2004, 11(6):522-533.
Hirao, L.A. et al., "Intradermal/subcutaneous immunization by electroporation improved . . . pigs and rhesus macaques", Vaccine, 2008, 26(3):440-448.
Yan, J. et al., "Enhanced cellular immune responses elicited by an engineered HIV-1 subtype B consensus-based envelope DNA vaccine", Mol Ther, 2007, 15(2):411-421.
Rao et al., "Multivalent HA DNA Vaccination Protects against Highly Pathogenic H5N1 Avian Influenza Infection in Chickens and Mice," PloS One, 2008, 3(6):e2432-1-e2432-10.
GenBank database entry ACP41934.1.
GenBank database entry ABO52797.1.
GenBank database entryABL77354.1.

* cited by examiner

INFLUENZA NUCLEIC ACID MOLECULES AND VACCINES MADE THEREFROM

CROSS-REFERENCE TO RELATED APPLICATIONS

This application is a divisional of U.S. patent application Ser. No. 12/694,238, filed on Jan. 26, 2010, allowed, which is incorporated herein by reference in its entirety.

FIELD OF THE INVENTION

The present invention relates to improved influenza viral vaccines, improved methods for inducing immune responses against influenza, improved methods for diagnosing vaccinated vs. infected influenza mammalian hosts and for prophylactically and/or therapeutically immunizing individuals against influenza.

BACKGROUND OF THE INVENTION

Influenza, commonly referred to as the flu, is an infectious disease caused by RNA viruses of the family Orthomyxoviridae. Influenza or flu viruses infect birds and mammals. Three of the five genera of Orthomyxoviridae are influenza viruses: Influenza A, Influenza B and Influenza C. Of these, Influenza A is the most common.

Influenza is typically transmitted through the air in aerosols produced by coughs or sneezes and by direct contact with body fluids containing the virus or contaminated surfaces. Seasonal epidemics of influenza occur worldwide and result in hundreds of thousands of deaths annually. In some years, pandemics occur and cause millions of deaths. In addition, livestock, particularly poultry and swine, are also susceptible to annual epidemics and occasional pandemics which cause large numbers of animal deaths and monetary losses.

Structurally, influenza viruses are similar, having generally spherical or filamentous virus particles of about 80-120 nm made up of similar molecular component. A central core comprising viral proteins and viral RNA is covered by a viral envelope made up of two different glycoproteins and a lipid coat derived from the cell that the viral particle is produced in. Two additional different glycoproteins are anchored within the viral envelope and include portions which project outward on the surface.

The influenza virus RNA genome is typically provided as eight different single stranded, negative sense RNA segments that together make up the genome's eleven viral genes which encode the eleven proteins (HA, NA, NP, M1, M2, NS1, NEP, PA, PB1, PB1-F2, PB2). The eight RNA segments are: 1) HA, which encodes hemagglutinin (about 500 molecules of hemagglutinin are needed to make one virion); 2) NA, which encodes neuraminidase (about 100 molecules of neuraminidase are needed to make one virion); 3) NP, which encodes nucleoprotein; 4) M, which encodes two matrix proteins (the M1 and the M2) by using different reading frames from the same RNA segment (about 3000 matrix protein molecules are needed to make one virion); 5) NS, which encodes two distinct non-structural proteins (NS1 and NEP) by using different reading frames from the same RNA segment; 6) PA, which encodes an RNA polymerase; 7) PB1, which encodes an RNA polymerase and PB1-F2 protein (induces apoptosis) by using different reading frames from the same RNA segment; and 8) PB2, which encodes an RNA polymerase.

Of these eleven proteins, hemagglutinin (HA) and neuraminidase (NA) are two large glycoproteins anchored in the viral envelope and present on the outer surface of the viral particles. These proteins serve as immunogens for immune responses against influenza. HA, which is a lectin that mediates binding of the virus to target cells and entry of the viral genome into the target cell, is expressed as a single gene product, HAD, and later processed by host proteases to produce two subunits, HA1 and HA2, which together form a complex on the surface of influenza viral particles. NA is involved in the release of newly produced mature viral particles produced in infected cells.

There are sixteen known HA serotypes and nine known NA serotypes for Influenza A viruses. The identity of the different serotypes present in a viral particle typically is used to describe a virus. For example, H1N1 is an influenza virus with HA serotype H1 and NA serotype N1; H5N1 is an influenza virus with HA serotype H5 and NA serotype N1. Only H1, H2 and H3 serotypes, and N1 and N2 serotypes usually infect humans.

Influenza strains are generally species or genus specific; i.e. an influenza strain which can infect pigs (a swine influenza virus) typically does not infect humans or birds; an influenza strain which can infect birds (an avian influenza virus) does not infect humans or pigs; and an influenza strain which can infect humans (a human influenza virus) does not infect birds or pigs. Influenza strains, however, can mutate and become infective from one species to another. For example, a strain which only infects pigs, a swine influenza, can mutate or recombine to become a strain that can infect humans only or both pigs and humans. A flu virus commonly referred to as "swine flu" is an influenza virus strain, such as an H1N1 strain, which can infect humans and which was derived from a strain that was previously specific for pigs (i.e. a swine flu virus is a swine origin human influenza or swine derived human influenza). A flu virus commonly referred to as "bird flu" is an influenza virus strain, such as an H5N1 strain, which can infect humans and which was derived from a strain that was previously specific for birds (i.e. a bird flu virus avian origin human influenza or avian derived human influenza).

Vaccinations against influenza are provided seasonally to many humans in developed countries and sometime to livestock. The vaccines used are limited in their protective results because the immune responses induced by the vaccines are specific for certain subtypes of virus. Different influenza vaccines are developed and administered annually based upon international surveillance and scientists' estimations of which types and strains of viruses will circulate in a given year. The virus changes significantly by mutation, recombination and reassortment of the segments. Thus, vaccines given in one year are not considered protective against the seasonal strains that are widely transmitted the following year.

The "flu shot" commonly promoted U.S. Centers for Disease Control and Prevention usually contains three killed/inactivated influenza viruses: one A (H3N2) virus, one A (H1N1) virus, and one B virus. Thus, it is apparent that vaccinations are limited to predictions of subtypes, and the availability of a specific vaccine to that subtype.

The direct administration of nucleic acid sequences to vaccinate against animal and human diseases has been studied and much effort has focused on effective and efficient means of nucleic acid delivery in order to yield necessary expression of the desired antigens, resulting immunogenic response and ultimately the success of this technique.

DNA vaccines have many conceptual advantages over more traditional vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platform's immunogenicity when moving to larger animals [Liu, M. A. and J. B. Ulmer, Human clinical trials of plasmid DNA vaccines. Adv Genet, 2005. 55: p. 25-40]. Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. In addition, studies have suggested that the use of consensus immunogens can be able to increase the breadth of the cellular immune response as compared to native antigens alone [Yan, J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

One method for delivering nucleic acid sequences such as plasmid DNA is the electroporation (EP) technique. The technique has been used in human clinical trials to deliver anticancer drugs, such as bleomycin, and in many preclinical studies on a large number of animal species.

There remains a need for an immunogenic influenza consensus hemagglutinin protein, for nucleic acid constructs that encode such a protein and for compositions useful to induce immune responses against multiple strains of influenza. There remains a need for effective vaccines against influenza that are economical and effective across numerous influenza subtypes for treating individuals.

SUMMARY OF THE INVENTION

Provided herein are isolated nucleic acid molecules comprising a nucleic acid sequence selected from the group consisting of: SEQ ID NO:1, a nucleic acid sequence that is 95% homologous to SEQ ID NO:1; a fragment of SEQ ID NO:1; a nucleic acid sequence that is 95% homologous to a fragment of SEQ ID NO: 1; SEQ ID NO:3; a nucleic acid sequence that is 95% homologous to SEQ ID NO:3; a fragment of SEQ ID NO:3; a nucleic acid sequence that is 95% homologous to a fragment of SEQ ID NO:3; SEQ ID NO:6; a nucleic acid sequence that is 95% homologous to SEQ ID NO:6; a fragment of SEQ ID NO:6; a nucleic acid sequence that is 95% homologous to a fragment of SEQ ID NO:6; SEQ ID NO:9, a nucleic acid sequence that is 95% homologous to SEQ ID NO:9; a fragment of SEQ ID NO:9; a nucleic acid sequence that is 95% homologous to a fragment of SEQ ID NO:9; SEQ ID NO:11, a nucleic acid sequence that is 95% homologous to SEQ ID NO: 11; a fragment of SEQ ID NO: 11; a nucleic acid sequence that is 95% homologous to a fragment of SEQ ID NO:11; SEQ ID NO:13; a nucleic acid sequence that is 95% homologous to SEQ ID NO:13; a fragment of SEQ ID NO:13; a nucleic acid sequence that is 95% homologous to a fragment of SEQ ID NO:13; and SEQ ID NO:15; a nucleic acid sequence that is 95% homologous to SEQ ID NO:15; a fragment of SEQ ID NO:15; a nucleic acid sequence that is 95% homologous to a fragment of SEQ ID NO:15.

Also provided are compositions comprising: a) a first nucleic acid sequence selected from the group consisting of one or more of: SEQ ID NO:1, a nucleic acid sequence that is 95% homologous to SEQ ID NO:1; a fragment of SEQ ID NO:1; a nucleic acid sequence that is 95% homologous to a fragment of SEQ ID NO: 1; SEQ ID NO:3; a nucleic acid sequence that is 95% homologous to SEQ ID NO:3; a fragment of SEQ ID NO:3; a nucleic acid sequence that is 95% homologous to a fragment of SEQ ID NO:3; SEQ ID NO:6; a nucleic acid sequence that is 95% homologous to SEQ ID NO:6; a fragment of SEQ ID NO:6; a nucleic acid sequence that is 95% homologous to a fragment of SEQ ID NO:6; SEQ ID NO:9; a nucleic acid sequence that is 95% homologous to SEQ ID NO:9; a fragment of SEQ ID NO:9; a nucleic acid sequence that is 95% homologous to a fragment of SEQ ID NO:9; SEQ ID NO:11; a nucleic acid sequence that is 95% homologous to SEQ ID NO: 11; a fragment of SEQ ID NO: 11; and a nucleic acid sequence that is 95% homologous to a fragment of SEQ ID NO: 11 SEQ ID NO:13; a nucleic acid sequence that is 95% homologous to SEQ ID NO:13; a fragment of SEQ ID NO:13; a nucleic acid sequence that is 95% homologous to a fragment of SEQ ID NO:13; SEQ ID NO:15; a nucleic acid sequence that is 95% homologous to SEQ ID NO:15; a fragment of SEQ ID NO:15; and a nucleic acid sequence that is 95% homologous to a fragment of SEQ ID NO:15; and b) a second nucleic acid sequence that encodes a protein selected from the group consisting of one or more of: influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin, neuraminidase and fragments thereof.

Some aspects of the invention provide methods of inducing an immune response comprising the step of: administering to an individual such nucleic acid molecules and/or compositions.

Additional aspects of the invention provide methods of protecting an individual against infection. The methods comprise the step of: administering to said individual a prophylactically effective amount of a nucleic acid molecule comprising such nucleic acid sequence or compositions; wherein the nucleic acid sequence is expressed in cells of said individual and a protective immune response is induced against a protein encoded by said nucleic acid sequence. In some embodiment, the immune response is a protective immune response against swine origin human influenza.

In some aspects of the invention, methods are provided for treating an individual who has been infected by Influenza. The methods comprise the step of: administering to said individual a therapeutically effective amount of such nucleic acid molecules and/or composition. In some embodiment, the immune response is a therapeutic immune response against swine origin human influenza.

Based upon the sequence of pVAX1 available from Invitrogen, the following mutations were found in the sequence of pVAX1 that was used as the backbone for pGX2009:

C>G 241 in CMV promoter

C>T 1942 backbone, downstream of the bovine growth hormone polyadenylation signal (bGHpolyA)

A>–2876 backbone, downstream of the Kanamycin gene

C>T 3277 in pUC origin of replication (Ori) high copy number mutation (see Nucleic Acid Research 1985)

G>C 3753 in very end of pUC Ori upstream of RNASeH site

Base pairs 2, 3 and 4 are changed from ACT to CTG in backbone, upstream of CMV promoter.

Figure 2:
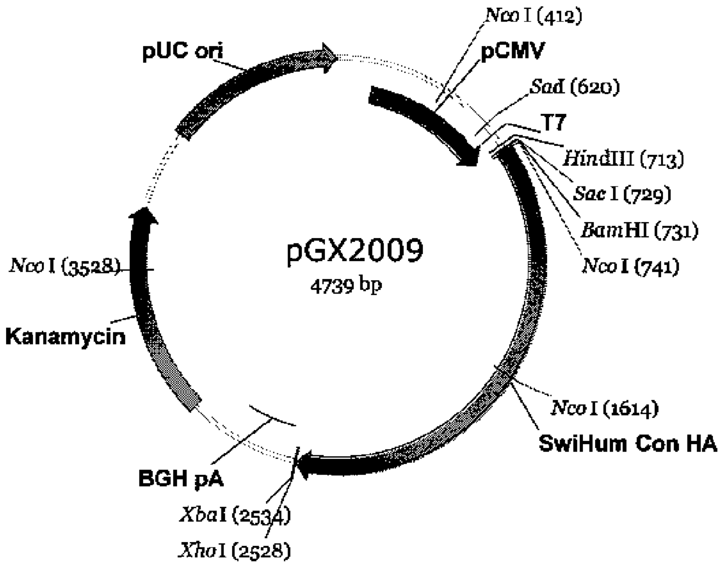
Figure 2:
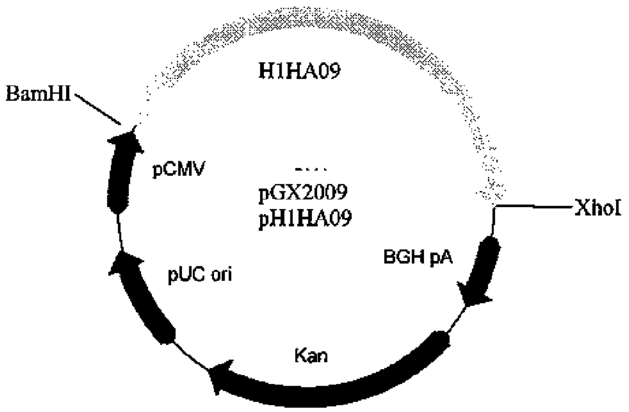

FIG. 2 shows two maps of the plasmid pGX2009, which is also referred to as pH1HA09. The nucleic acid sequence of the plasmid pGX2009 (SEQ ID NO:5) includes the coding sequence for the consensus H1 protein construct (amino acid SEQ ID NO:4 encoded by SEQ ID NO:3) which includes the IgE leader (amino acid SEQ ID NO: 17) linked to the N terminal of the consensus H1 amino acid sequence (amino acid SEQ ID NO:2 encoded by SEQ ID NO:1) which is linked at its C terminal to the HA Tag (SEQ ID NO:18). The consensus H1 protein (amino acid SEQ ID NO:4 encoded by SEQ ID NO:3) is labeled SwiHum Con HA and H1HA09.

Figure 3:
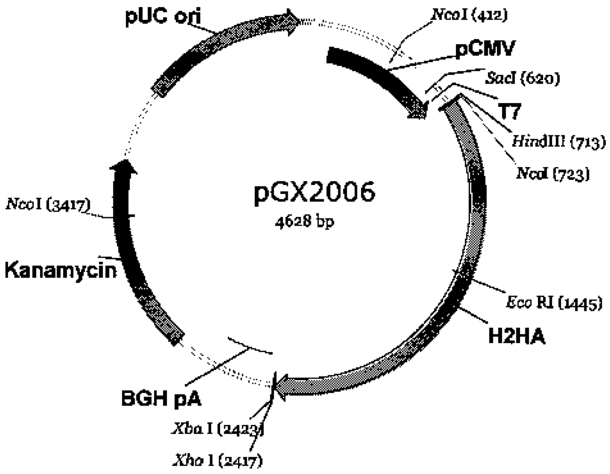

FIG. 3 shows a maps of the plasmid pGX2006. The nucleic acid sequence of the plasmid pGX2006 (SEQ ID NO:8) includes the coding sequence for consensus H2 protein (amino acid SEQ ID NO:7 encoded by SEQ ID NO:6) which is labeled H2HA.

Figure 4:
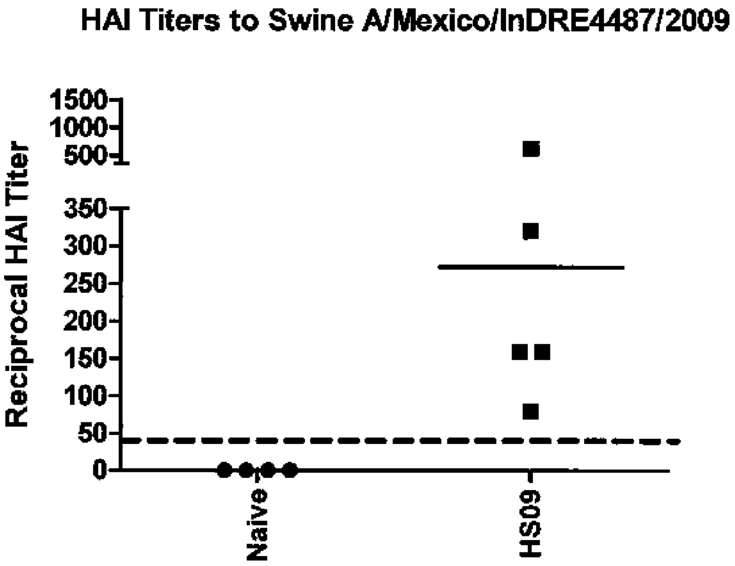

FIG. 4 shows data from hemagglutination inhibition assays performed with sera from immunized ferrets.

Figure 5:
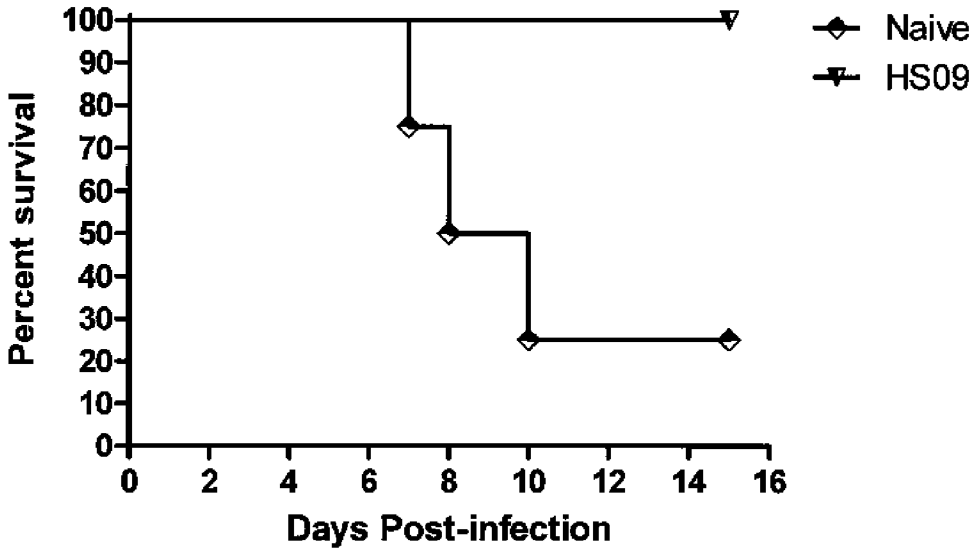

FIG. 5 shows results of a challenge of immunized and unimmunized ferrets with a novel H1N1 strain.

DETAILED DESCRIPTION

Consensus amino acid sequences of each of influenza A H1 and H2 (referred to herein as “consensus H1” (SEQ ID NO:2) and “consensus H2” (SEQ ID NO:7), respectively), as well as a novel synthetic hybrid consensus H1 influenza A hemagglutinin amino acid sequence (referred to herein as “consensus U2” (SEQ ID NO: 10)) and a consensus amino acid sequence of influenza B hemagglutinin (referred to herein as “consensus BHA” (SEQ ID NO:13)) are provided, which can provide protection of mammals against influenza. In addition, proteins are provided which comprise the consensus H1 amino acid sequence, the consensus H2 amino acid sequence, the consensus U2 amino acid sequence and/or the consensus BHA amino acid sequence. In some aspects, nucleic acid sequences are provided which encode proteins comprising the consensus H1 amino acid sequence (for example (SEQ ID NO:1) or (SEQ ID NO:3)), the consensus H2 amino acid sequence (for example (SEQ ID NO:6)), the consensus U2 amino acid sequence (for example (SEQ ID NO:9) or (SEQ ID NO: 11)), and/or the consensus BHA amino acid sequence (for example (SEQ ID NO:13) or (SEQ ID NO: 15)).

While not being bound by scientific theory, a vaccine that can be used to elicit an immune response (humoral, cellular, or both) broadly against multiple influenza subtypes may comprise one or more of the following: 1) a nucleic acid sequence that encodes a protein comprising the consensus H1 amino acid sequence; 2) a protein comprising the consensus H1 amino acid sequence; 3) a nucleic acid sequence that encodes a protein comprising the consensus H2 amino acid sequence; 4) a protein comprising the consensus H2 amino acid sequence; 5) a nucleic acid sequence that encodes a protein comprising the consensus U2 amino acid sequence; 6) a protein comprising the consensus U2 amino acid sequence; 7) a nucleic acid sequence that encodes a protein comprising the consensus BHA amino acid sequence; and 8) a protein comprising the consensus BHA amino acid sequence.

Immunization methods can be performed and vaccines can be prepared which use and/or combine two or more of the following components: 1) a nucleic acid sequence that encodes a protein comprising the consensus H1 amino acid sequence; 2) a protein comprising the consensus H1 amino acid sequence; 3) a nucleic acid sequence that encodes a protein comprising the consensus H2 amino acid sequence, 4) a protein comprising the consensus H2 amino acid sequence; 5) a nucleic acid sequence that encodes a protein comprising the consensus U2 amino acid sequence, 6) a protein comprising the consensus U2 amino acid sequence, 7) a nucleic acid sequence that encodes a protein comprising the consensus BHA amino acid sequence, and 8) a protein comprising the consensus BHA amino acid sequence. For more broad based treatments against influenza, immunization methods can be performed and vaccines can be prepared which use and/or combine one or more other influenza proteins such as influenza A H1-H16, influenza A N1-N9, influenza B hemagglutinin, influenza B neuraminidase and/or genes encoding these proteins together with one or more of the following components: 1) a nucleic acid sequence that encodes a protein comprising the consensus H1 amino acid sequence; 2) a protein comprising the consensus H1 amino acid sequence; 3) a nucleic acid sequence that encodes a protein comprising the consensus H2 amino acid sequence, 4) a protein comprising the consensus H2 amino acid sequence; 5) a nucleic acid sequence that encodes a protein comprising the consensus U2 amino acid sequence, 6) a protein comprising the consensus U2 amino acid sequence, 7) a nucleic acid sequence that encodes a protein comprising the consensus BHA amino acid sequence, and 8) a protein comprising the consensus BHA amino acid sequence.

1. DEFINITIONS

The terminology used herein is for the purpose of describing particular embodiments only and is not intended to be limiting. As used in the specification and the appended claims, the singular forms “a,” “an” and “the” include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

“Adjuvant” as used herein means any molecule added to the DNA plasmid vaccines described herein to enhance the immunogenicity of the antigens encoded by the DNA plasmids and the encoding nucleic acid sequences described hereinafter.

b. Antibody

“Antibody” as used herein means an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

“Coding sequence” or “encoding nucleic acid” as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to whom the nucleic acid is administered.

d. Complement

“Complement” or “complementary” as used herein means a nucleic acid can mean Watson-Crick (e.g., A-T/U and C-G) or Hoogsteen base pairing between nucleotides or nucleotide analogs of nucleic acid molecules.

e. Consensus or Consensus Sequence

“Consensus” or “consensus sequence” as used herein means a polypeptide sequence based on analysis of an alignment of multiple subtypes of a particular influenza antigen. Nucleic acid sequences that encode a consensus polypeptide sequence may be prepared. Vaccines comprising proteins that comprise consensus sequences and/or nucleic acid molecules that encode such proteins can be used to induce broad immunity against multiple subtypes or serotypes of a particular influenza antigen. Consensus influenza antigens can include influenza A consensus hemagglutinin amino acid sequences, including for example consensus H1, consensus H2, or influenza B consensus hemagglutinin amino acid sequences.

f. Constant Current

“Constant current” as used herein means a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

“Current feedback” or “feedback” can be used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback can be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop can be instantaneous as it is an analog closed-loop feedback.

h. Decentralized Current

“Decentralized current” as used herein means the pattern of electrical currents delivered from the various needle electrode arrays of the electroporation devices described herein, wherein the patterns minimize, or preferably eliminate, the occurrence of electroporation related heat stress on any area of tissue being electroporated.

i. Electroporation

“Electroporation,” “electro-permeabilization,” or “electro-kinetic enhancement” (“EP”) as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

j. Feedback Mechanism

“Feedback mechanism” as used herein means a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism can be performed by an analog closed loop circuit.

k. Fragment

“Fragment” as used herein with respect to nucleic acid sequences means a nucleic acid sequence or a portion thereof, that encodes a polypeptide capable of eliciting an immune response in a mammal that cross reacts with a full length wild type strain influenza antigen, including, e.g., an influenza A H1 hemagglutinin, an influenza A H2 hemagglutinin or an influenza B hemagglutinin. The fragments can be DNA fragments selected from at least one of the various nucleotide sequences that encode the consensus amino acid sequences and constructs comprising such sequences, including SEQ ID NOS: 1, 3, 6, 9, 11 13 and 15. DNA fragments can comprise coding sequences for the immunoglobulin leader such as IgE or IgG sequences. The DNA fragments can be 30 or more nucleotides in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, 720 or more, 780 or more, 840 or more, 900 or more, 960 or more, 1020 or more, 1080 or more, 1140 or more, 1200 or more, 1260 or more, 1320 or more, 1380 or more, 1440 or more, 1500 or more, 1560 or more, 1620 or more, 1680 or more, 1740 or more, 1800 or more, 1860 or more, 1820 or more, 1880 or more, 1940 or more, 2000 or more, 2600 or more, 2700 or more, 2800 or more, 2900 or more, 2910 or more, 2920 or more, 2930 or more, 2931 or more, 2932 or more, 2933 or more, 2934 or more, 2935 or more, 2936 or more, 2937 or more, or 2938 or more in length. DNA fragments can be fewer than 10 nucleotides, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 720, fewer than 780, fewer than 840, fewer than 900, fewer than 960, fewer than 1020, fewer than 1080, fewer than 1140, fewer than 1200, fewer than 1260, fewer than 1320, fewer than 1380, fewer than 1440, fewer than 1500, fewer than 1560, fewer than 1620, fewer than 1680, or fewer than 1740 nucleotides, fewer than 1800, fewer than 1860, fewer than 1820, fewer than 1880, fewer than 1940, fewer than 2000, fewer than 2600, fewer than 2700, fewer than 2800, fewer than 2900, fewer than 2910, fewer than 2920, fewer than 2930, fewer than 2931, fewer than 2932, fewer than 2933, fewer than 2934, fewer than 2935, fewer than 2936, fewer than 2937, or fewer than 2938.

"Fragment" with respect to polypeptide sequences means a polypeptide capable of eliciting an immune response in a mammal that cross reacts with a full length wild type strain influenza antigen, including, e.g., an influenza A H1 hemagglutinin, an influenza A H2 hemagglutinin or an influenza B hemagglutinin. The fragment can be polypeptide fragment selected from at least one of the various polypeptide sequences of the present invention, including SEQ ID NOS: 2, 4, 7, 10, 12, 14 and 16. Polypeptide fragments can be analyzed to contact at least one antigenic epitope as provided by a publicly available database such as the Los Alamos National Laboratory's HA Sequence Database. Polypeptides HA fragments can further comprise amino acid sequences for the immunoglobulin leader such as IgE or IgG. The polypeptide fragments can be 30 or more amino acids in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, or 710 amino acids or more in length. Polypeptide fragments can be fewer than 10 amino acids, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 700, fewer than 701, fewer than 702, fewer than 703, fewer than 704, fewer than 705, fewer than 706, fewer than 707, fewer than 708, fewer than 709, or fewer than 710 amino acids in length.

l. Genetic Construct

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

m. Identical

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

n. Impedance

"Impedance" can be used when discussing the feedback mechanism and can be converted to a current value according to Ohm's law, thus enabling comparisons with the preset current.

o. Immune Response

"Immune response" as used herein means the activation of a host's immune system, e.g., that of a mammal, in response to the introduction of antigen such as an influenza hemagglutinin consensus antigen. The immune response can be in the form of a cellular or humoral response, or both.

p. Nucleic Acid

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

q. Operably Linked

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

r. Promoter

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

s. Stringent Hybridization Conditions

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

t. Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or that the two sequences hybridize under stringent hybridization conditions.

u. Substantially Identical

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or with respect to nucleic acids, if the first sequence is substantially complementary to the complement of the second sequence.

v. Subtype or Serotype

"Subtype" or "serotype": as used herein, interchangeably, and in reference to influenza virus, means genetic variants of an influenza virus such that one subtype is recognized by an immune system apart from a different subtype.

w. Variant

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

x. Vector

"Vector" as used herein means a nucleic acid sequence containing an origin of replication. A vector can be a vector, bacteriophage, bacterial artificial chromosome or yeast artificial chromosome. A vector can be a DNA or RNA vector. A vector can be a self-replicating extrachromosomal vector, and preferably, is a DNA plasmid.

2. INFLUENZA ANTIGEN

Provided herein are antigens capable of eliciting an immune response in a mammal against one or more influenza serotypes. The antigen can be capable of eliciting an immune response in a mammal against one or more influenza serotypes, including against one or more pandemic strains, such as 2009 H1N1 swine originated influenza. The antigen can be capable of eliciting an immune response in a mammal against one or more influenza serotype, including against one or more strains of swine derived human influenza. The antigen can comprise epitopes that make them particularly effective as immunogens against which anti-influenza immune responses can be induced.

The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B. The antigen can contain at least one antigenic epitope that can be effective against particular influenza immunogens against which an immune response can be induced. The antigen may provide an entire repertoire of immunogenic sites and epitopes present in an intact influenza virus. The antigen may be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen may be a hybrid consensus hemagglutinin antigen sequence that can be derived from combining two different consensus hemagglutinin antigen sequences or portions thereof. Each of two different consensus hemagglutinin antigen sequences may be derived from a different set of a plurality of influenza A virus strains of one serotype such as a plurality of influenza A virus strains of serotype H1. The antigen may be a consensus hemagglutinin antigen sequence that can be derived from hemagglutinin antigen sequences from a plurality of influenza B virus strains.

The consensus hemagglutinin antigen may be a protein comprising SEQ ID NO: 2 (the consensus H1 amino acid sequence) wherein amino acids 1-343 correspond to the HA1 subunit of the precursor HA0 consensus H1 amino acid sequence and amino acids 344-566 correspond to the HA2 subunit of the HA0 consensus H1 amino acid sequence. The consensus hemagglutinin antigen may be a protein comprising SEQ ID NO: 7 (the consensus H2 amino acid sequence). The consensus hemagglutinin antigen may be a synthetic hybrid consensus H1 sequences comprising portions of two different consensus H1 sequences which are each derived from a different set of sequences from the other. An example of a consensus HA antigen that is a synthetic hybrid consensus H1 protein is a protein comprising SEQ ID NO: 10 (the U2 amino acid sequence). The consensus hemagglutinin antigen may be a consensus hemagglutinin protein derived from hemagglutinin sequences from influenza B strains, such as a protein comprising SEQ ID NO: 14 (the consensus BHA amino acid sequence).

The consensus hemagglutinin antigen may further comprise one or more additional amino acid sequence elements. The consensus hemagglutinin antigen may further comprise on its N-terminal an IgE or IgG leader amino acid sequence. The IgE leader amino acid sequence may be SEQ ID NO: 17. The consensus hemagglutinin antigen may further comprise an immunogenic tag which is a unique immunogenic epitope that can be detected by readily available antibodies. An example of such an immunogenic tag is the 9 amino acid influenza HA Tag which may be linked on the consensus hemagglutinin C terminus. The HA Tag amino acid sequence may be SEQ ID NO:18. In some embodiments, consensus hemagglutinin antigen may further comprise on its N-terminal an IgE or IgG leader amino acid sequence and on its C terminal an HA tag.

The consensus hemagglutinin antigen may be a consensus hemagglutinin protein that consists of consensus influenza amino acid sequences or fragments and variants thereof. The consensus hemagglutinin antigen may be a consensus hemagglutinin protein that comprises non-influenza protein sequences and influenza protein sequences or fragments and variants thereof.

Examples of a consensus H1 protein include those that may consist of the consensus H1 amino acid sequence (SEQ ID NO:2) or those that further comprise additional elements such as an IgE leader sequence, or an HA Tag or both an IgE leader sequence and an HA Tag. An example of the consensus H1 protein that includes both an IgE leader sequence and an HA Tag is SEQ ID NO: 4, which comprises the consensus H1 amino acid coding sequence (SEQ ID NO:2) linked to the IgE leader amino acid sequence (SEQ ID NO: 17) at its N terminal and linked to the HA Tag (SEQ ID NO: 18) at its C terminal.

Examples of consensus H2 proteins include those that may consist of the consensus H2 amino acid sequence (SEQ ID NO:7) or those that further comprise an IgE leader sequence, or an HA Tag, or both an IgE leader sequence and an HA Tag.

Examples of hybrid consensus H1 proteins include those that may consist of the consensus U2 amino acid sequence (SEQ ID NO:10) or those that further comprise an IgE leader sequence, or an HA Tag, or both an IgE leader sequence and an HA Tag. An example of the consensus U2 protein is SEQ ID NO:12, which comprises the consensus U2 amino acid sequence (SEQ ID NO: 10) linked to the IgE leader amino acid sequence (SEQ ID NO: 17) at its N terminal and linked to the HA Tag (SEQ ID NO:18) at its C terminal.

Examples of hybrid consensus influenza B hemagglutinin proteins include those that may consist of the consensus BHA amino acid sequence (SEQ ID NO: 14) or it may comprise an IgE leader sequence, or a an HA Tag, or both an IgE leader sequence and an HA Tag. An example of the consensus BHA protein is SEQ ID NO:16 which comprises the consensus BHA amino acid sequence (SEQ ID NO: 14) linked to the IgE leader amino acid sequence (SEQ ID NO: 17) at its N terminal and linked to the HA Tag (SEQ ID NO: 18) at its C terminal.

The consensus hemagglutinin protein can be encoded by a consensus hemagglutinin nucleic acid, a variant thereof or a fragment thereof. Unlike the consensus hemagglutinin protein which may be a consensus sequence derived from a plurality of different hemagglutinin sequences from different strains and variants, the consensus hemagglutinin nucleic acid refers to a nucleic acid sequence that encodes a consensus protein sequence and the coding sequences used may differ from those used to encode the particular amino acid sequences in the plurality of different hemagglutinin sequences from which the consensus hemagglutinin protein sequence is derived. The consensus nucleic acid sequence may be codon optimized and/or RNA optimized. The consensus hemagglutinin nucleic acid sequence may comprise a Kozak's sequence in the 5' untranslated region. The consensus hemagglutinin nucleic acid sequence may comprise nucleic acid sequences that encode a leader sequence. The coding sequence of an N terminal leader sequence is 5' of the hemagglutinin coding sequence. The N-terminal leader can be facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C terminus of the protein and the sequence encoding it is 3' of the HA coding sequence. The immunogenic tag provides a unique epitope for which there are readily available antibodies so that such antibodies can be used in assays to detect and confirm expression of the protein. The immunogenic tag can be an H Tag at the C-terminus of the protein.

Consensus hemagglutinin nucleic acid may have a polynucleotide sequence that encodes a protein that comprises the amino acid sequence of SEQ ID NO: 2, SEQ ID NO:7, SEQ ID NO:10 or SEQ ID NO:14. A consensus hemagglutinin nucleic acid that encodes SEQ ID NO: 2, SEQ ID NO:7, SEQ ID NO: 10 or SEQ ID NO:14 may be SEQ ID NO: 1, SEQ ID NO:6, SEQ ID NO:9 or SEQ ID NO: 13, respectively. The consensus hemagglutinin nucleic acid can further comprise a polynucleotide sequence encoding the IgE leader amino acid sequence, or a polynucleotide sequence encoding an HA Tag amino acid sequence, or both. SEQ ID NO: 17 is an IgE leader polypeptide sequence. SEQ ID NO: 18 is an HA Tag polypeptide sequence. Examples of hemagglutinin consensus nucleic acids that further comprise polynucleotide sequences encoding an IgE leader sequence and an HA Tag include nucleic acid molecules that encode proteins that comprise the amino acid sequence of SEQ ID NO:4, SEQ ID NO: 12 or SEQ ID NO: 16. A consensus hemagglutinin nucleic acid that encodes SEQ ID NO:4, SEQ ID NO: 12 or SEQ ID NO: 16 may be SEQ ID NO:3, SEQ ID NO: 11 or SEQ ID NO: 15, respectively.

3. GENETIC CONSTRUCTS AND PLASMIDS

Provided herein are genetic constructs that can comprise a nucleic acid sequence that encodes the hemagglutinin antigen. The genetic construct can be present in the cell as a functioning extrachromosomal molecule comprising the nucleic acid encoding the hemagglutinin antigen. The genetic construct comprising the nucleic acid encoding the hemagglutinin antigen can be linear minichromosome including centromere, telomers or plasmids or cosmids.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the hemagglutinin nucleic acid. The regulatory elements can be a promoter, an enhacer an initiation codon, a stop codon, or a polyadenylation signal.

Compositions may comprise a first nucleic acid sequence which encodes the hemagglutinin consensus antigen selected from the group consisting of one or more of: influenza A consensus hemagglutinin H1 antigen, influenza A consensus hemagglutinin H2 antigen, influenza A consensus hemagglutinin U2 antigen, and influenza B consensus hemagglutinin protein BHA, and may further comprise one or more additional nucleic acid sequence(s) that encodes one or more protein(s) selected from the group consisting of: influenza A hemagglutinin proteins H1, H2, H3, H4, H5, H6, H7, H8, H9, H10, H11, H12, H13, H14, H15, H16, influenza A neuraminidase N1, N2, N3, N4, N5, N6, N7, N8, N9, influenza B hemagglutinin (BHA) and influenza B neuraminidase (BNA). The first and additional nucleic acid sequences may be present on the same nucleic acid molecule or different nucleic acid molecules. The first and additional nucleic acid sequences can be under the control of regulatory elements that function in a human cell. The additional coding sequence may encode one or more H1, H2, H3, H4, H5, H6, H7, H8, H9, H10, H11, H12, H13, H14, H15, H16, N1, N2, N3, N4, N5, N6, N7, N8, N9, BHA and BNA from one or more strains of influenza, or be a consensus derived from a plurality of strains having the serotype, or be a hybrid which includes sequences from two or more consensus sequences.

The nucleic acid sequences may make up a genetic construct that can be a vector. The vector can be capable of expressing a consensus hemagglutinin antigen in the cell of a mammal in a quantity effective to elicit an immune response in the mammal. The vector can be recombinant. The vector can comprise heterologous nucleic acid encoding the consensus hemagglutinin antigen. The vector can be a plasmid. The vector can be useful for transfecting cells with nucleic acid encoding a consensus hemagglutinin antigen, which the transformed host cell is cultured and maintained under conditions wherein expression of the consensus hemagglutinin antigen takes place.

The vector can comprise heterologous nucleic acid encoding a consensus hemagglutinin antigen and can further comprise an initiation codon, which can be upstream of the consensus hemagglutinin coding sequence, and a stop codon, which can be downstream of the consensus hemagglutinin coding sequence. The initiation and termination codon can be in frame with the consensus hemagglutinin coding sequence. The vector can also comprise a promoter that is operably linked to the consensus hemagglutinin coding sequence. The promoter operably linked to the consensus hemagglutinin coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the HA coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the consensus hemagglutinin coding. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

Figure 1:
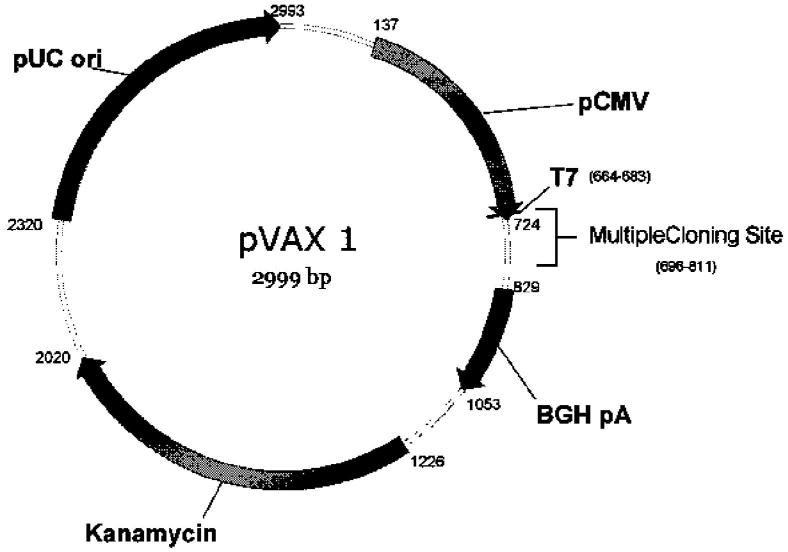
FIG. 1 is a map of the 2999 basepair backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The vector can also comprise a mammalian origin of replication in order to maintain the vector extrachromosomally and produce multiple copies of the vector in a cell. The vector can be pVAX1 (FIG. 1), pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 with changes such as those described in the paragraph referring to FIG. 1 in the Brief Description of the Figures section above. The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The consensus hemagglutinin coding sequence can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which maybe used for protein production in mammalian cells such as Chinese hamster ovary (CHO) cells. The vector can be expression vectors or systems to produce protein by routine techniques and readily available starting materials including Sambrook et al., Molecular Cloning an Laboratory Manual, Second Ed., Cold Spring Harbor (1989), which is incorporated fully by reference.

The vector can be pGX2009 or pGX2006, which can be used for expressing the consensus hemagglutinin antigen. The vector pGX2009 (4739 bp, FIG. 2; SEQ ID NO: 5) is a modified pVAX1 plasmid with a nucleic acid sequence that encodes a consensus H1 protein (amino acid SEQ ID NO:4 encoded by SEQ ID NO:3) that comprises an IgE leader sequence (amino acid SEQ ID NO: 12 encoded by SEQ ID NO:11) linked to a consensus H1 amino acid sequence (amino acid SEQ ID NO:2 encoded by SEQ ID NO:1). The vector pGX2006 (4628 bp; FIG. 3, SEQ ID NO:8) is a pVAX1 plasmid with a nucleic acid sequence that encodes a consensus H2 protein (amino acid SEQ ID NO:7 encoded by SEQ ID NO:6).

The genetic constructs and components disclosed herein which include consensus hemagglutinin coding sequences may be used to express other influenza proteins such as influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin or neuraminidase protein whereby coding sequences for influenza A proteins H1, H2, H3, H4, H5, H6, H7, H8, H9, H10, H11, H12, H13, H14, H15, H16, N1, N2, N3, N4, N5, N6, N7, N8, N9, influenza B hemagglutinin or neuraminidase protein are included in place of consensus hemagglutinin coding sequences.

4. PHARMACEUTICAL COMPOSITIONS

Provided herein are pharmaceutical compositions according to the present invention which comprise about 1 nanogram to about 10 mg of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or mg. In some embodiments, pharmaceutical compositions according to the present invention comprise about 5 nanogram to about 10 mg of DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Preferably the pharmaceutical composition is a vaccine, and more preferably a DNA vaccine.

Provided herein is a vaccine capable of generating in a mammal an immune response against one or more influenza serotypes. The vaccine can comprise the genetic construct as discussed above. The vaccine can comprise a plurality of the vectors each directed to one or more Influenza A serotypes such as H1-H16 Influenza B hemagglutinin or combinations thereof. The vaccine may comprise one or more nucleic acid sequences that encode one or more consensus hemagglutinin antigens. When the vaccine comprises more than one consensus hemagglutinin nucleic acid sequences, all such sequences may be present on a single nucleic acid molecule or each such sequences may be present on a different nucleic acid molecule. Alternatively, vaccines that comprise more than one consensus hemagglutinin nucleic acid sequences may comprise nucleic acid molecules with a single consensus hemagglutinin nucleic acid sequences and nucleic acid molecules with more than one consensus hemagglutinin nucleic acid sequences. In addition, vaccines comprising one or more consensus hemagglutinin nucleic acid sequences may further comprise coding sequences for one or more proteins selected from the group consisting of H1, H2, H3, H4, H5, H6, H7, H8, H9, H10, H11, H12, H13, H14, H15, H16, N1, N2, N3, N4, N5, N6, N7, N8, N9 and influenza B neuraminise.

In some embodiments, vaccines may comprise proteins. Some vaccines may comprise one or more consensus hemagglutinin antigens such as H1, H2, U2 and BHA. The vaccines may comprise one or more other proteins selected from the group consisting of H1, H2, H3, H4, H5, H6, H7, H8, H9, H10, H11, H12, H13, H14, H15, H16, N1, N2, N3, N4, N5, N6, N7, N8, N9 and influenza B neuraminidase. The vaccines may comprise one or more consensus hemagglutinin antigens in combination with one or more other proteins selected from the group consisting of H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase.

The vaccine may be a DNA vaccine. The DNA vaccine may comprise a plurality of the same or different plasmids comprising one or more of consensus hemagglutinin nucleic acid sequences. The DNA vaccine may comprise one or more nucleic acid sequences that encode one or more consensus hemagglutinin antigens. When the DNA vaccine comprises more than one consensus hemagglutinin nucleic acid sequences, all such sequences may be present on a single plasmid, or each such sequences may be present on a different plasmids, or some plasmids may comprise a single consensus hemagglutinin nucleic acid sequences while other plasmids have more than one consensus hemagglutinin nucleic acid sequences. In addition, DNA vaccines may further comprise one or more consensus coding sequences for one or more proteins selected from the group consisting of influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin and neuramidase. Such additional coding sequences may be on the same or different plasmids from each other and from the plasmids comprising one or more of consensus hemagglutinin nucleic acid sequences.

In some embodiments, vaccines may comprise nucleic acid sequences that encode influenza antigens in combination with influenza antigens. In some embodiments, the nucleic acid sequences encode one or more consensus hemagglutinin antigens such as H1, H2, U2 and BHA. In some embodiments, the nucleic acid sequences encode one or more one or more other proteins selected from the group consisting of, influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin and neuramidase. In some embodiments, the vaccines comprise one or more consensus hemagglutinin antigens such as H1, H2, U2 and BHA. In some embodiments, the vaccines comprise one or more one or more other proteins selected from the group consisting of influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin and neuramidase.

In some embodiments, vaccines comprise a combination of three or more consensus hemagglutinin nucleic acid sequences including those encoding one or more of H1, H2, U2 and BHA. In some embodiments, vaccines comprise a combination of three or more hemagglutinin nucleic acid sequences including those encoding consensus U2, consensus BHA and an H3 hemagglutinin. In some embodiments, vaccines comprise a combination of three or more hemagglutinin nucleic acid sequences including those encoding consensus BHA, an H1 hemagglutinin and an H3 hemagglutinin. In some embodiments, vaccines comprise one or more nucleic acid sequences that encode one or more influenza antigens disclosed in U.S. Ser. No. 12/375,518, which is incorporated herein by reference and/or U.S. Ser. No. 12/269,824, which is incorporated herein by reference. In some embodiments, vaccines comprise a nucleic acid sequence that encodes an H1 hemagglutinin from U.S. Ser. No. 12/375,518 (SEQ ID NO:36 therein) and/or a nucleic acid sequence, SEQ ID NO:19, set forth herein, that encodes an H1 hemagglutinin. In some embodiments, vaccines comprise a nucleic acid sequence, SEQ ID NO:20 set forth herein, that encodes an H3 hemagglutinin.

In some embodiments, vaccines comprise a combination of three or more consensus hemagglutinin proteins including one or more of H1, H2, U2 and BHA. In some embodiments, vaccines comprise a combination of three or more hemagglutinin proteins including consensus U2, consensus BHA and an H3 hemagglutinin. In some embodiments, vaccines comprise a combination of three or more hemagglutinin proteins including consensus BHA, an H1 hemagglutinin and an H3 hemagglutinin. In some embodiments, vaccines comprise one or more antigens from U.S. Ser. No. 12/375,518 and/or U.S. Ser. No. 12/269,824. In some embodiments, vaccines comprise an H1 hemagglutinin disclosed in U.S. Ser. No. 12/375,518 (SEQ ID NO:37 therein) and/or U.S. Ser. No. 12/269,824 (SEQ ID NO: 10 therein). In some embodiments, vaccines comprise an H3 hemagglutinin disclosed in U.S. Ser. No. 12/269,824 (SEQ ID NO:12 therein).

In some embodiments, vaccines comprise a combination of 1) the consensus hemagglutinin U2 protein and/or a nucleic acid sequence encoding the consensus hemagglutinin U2 protein, 2) the consensus hemagglutinin BHA protein and/or a nucleic acid sequence encoding the consensus hemagglutinin BHA protein, and 3) a hemagglutinin H3 protein disclosed in U.S. Ser. No. 12/269,824 (SEQ ID NO:12 therein) and/or a nucleic acid sequence, SEQ ID NO:20 set forth herein, that encodes hemagglutinin H3 protein.

In some embodiments, vaccines comprise a combination of I) the consensus hemagglutinin BHA protein and/or a nucleic acid sequence encoding the consensus hemagglutinin BHA protein, 2) a hemagglutinin H1 protein disclosed in U.S. Ser. No. 12/269,824 (SEQ ID NO:10 therein) or U.S. Ser. No. 12/375,518 (SEQ ID NO:37 therein) and/or a nucleic acid sequence, SEQ ID NO:19 set forth herein, that encodes hemagglutinin H1 protein or U.S. Ser. No. 12/375,518 (SEQ ID NO:36 therein), and 3) a hemagglutinin H3 protein disclosed in U.S. Ser. No. 12/269,824 (SEQ ID NO: 12 therein) and/or a nucleic acid sequences encoding sequence, SEQ ID NO:20 set forth herein, that encodes hemagglutinin H3 protein.

DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome. The vaccine can be an RNA of the hemagglutinin antigen. The RNA vaccine can be introduced into the cell.

The vaccine can be a recombinant vaccine comprising the genetic construct or antigen described above. The vaccine can also comprise one or more consensus hemagglutinin antigen in the form of one or more protein subunits, one or more killed influenza particles comprising one or more consensus hemagglutinin antigens, or one or more attenuated influenza particles comprising one or more consensus hemagglutinin antigens. The attenuated vaccine can be attenuated live vaccines, killed vaccines and vaccines that use recombinant vectors to deliver foreign genes that encode one or more consensus hemagglutinin antigens, and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine can comprise vectors and/or proteins directed to Influenza A serotypes from particular regions in the world, for example, Asia. The vaccine can also be directed against Influenza A serotypes of swine origin that now infect humans. The vaccine can comprise vectors and/or proteins directed to Influenza B from particular regions in the world. The vaccine can also be directed against Influenza B that infect humans. The vaccine can comprise one or more vectors and/or one or more proteins directed to one or more strains of Influenza A and/or B.

The vaccine provided may be used to induce immune responses including therapeutic or prophylactic immune responses. Antibodies and/or killer T cells may be generated which are directed to the consensus hemagglutinin antigen, and also broadly across multiple subtypes of influenza viruses. Such antibodies and cells may be isolated.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine can further comprise a genetic vaccine facilitator agent as described in U.S. Serial No. 021,579 filed Apr. 1, 1994, which is fully incorporated by reference.

5. METHODS OF DELIVERY

Provided herein is a method for delivering the pharmaceutical formulations, preferably vaccines, for providing genetic constructs and proteins of the hemagglutinin antigen which comprise epitopes that make them particular effective immunogens against which an immune response to influenza viral infections can be induced. The method of delivering the vaccine, or vaccination, can be provided to induce a therapeutic and/or prophylactic immune response. The vaccination process can generate in the mammal an immune response against a plurality of influenza subtypes, including a H1N1 serotype, such as the 2009 swine originated H1N1, or other seasonal and/or pandemic varieties. The vaccine can be delivered to an individual to modulate the activity of the mammal's immune system and enhance the immune response. The delivery of the vaccine can be the transfection of the HA antigen as a nucleic acid molecule that is expressed in the cell and delivered to the surface of the cell upon which the immune system recognized and induces a cellular, humoral, or cellular and humoral response. The delivery of the vaccine can be use to induce or elicit and immune response in mammals against a plurality of influenza viruses by administering to the mammals the vaccine as discussed herein.

Upon delivery of the vaccine to the mammal, and thereupon the vector into the cells of the mammal, the transfected cells will express and secrete the corresponding influenza protein, including at least one of the consensus antigens, and preferably H1, H2, U2, and BHA. These secreted proteins, or synthetic antigens, will be recognized as foreign by the immune system, which will mount an immune response that can include: antibodies made against the antigens, and T-cell response specifically against the antigen. In some examples, a mammal vaccinated with the vaccines discussed herein will have a primed immune system and when challenged with an influenza viral strain, the primed immune system will allow for rapid clearing of subsequent influenza viruses, whether through the humoral, cellular, or both. The vaccine can be delivered to an individual to modulate the activity of the individual's immune system thereby enhancing the immune response.

The vaccine can be delivered in the form of a DNA vaccine and methods of delivering a DNA vaccines are described in U.S. Pat. Nos. 4,945,050 and 5,036,006, which are both incorporated fully by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

a. Combination Treatments

The pharmaceutical compositions, preferably vaccines, can be administered in combination with one or more other influenza proteins or genes encoding influenza A H1, H2, H3, H4, H5, H6, H7, H8, H9, H10, H11, H12, H13, H1114, H15, H16, N1, N2, N3, N4, N5, N6, N7, N8, N9, influenza B hemagglutinin and neuramidase. The vaccine can be administered in combination with proteins or genes encoding adjuvants, which can include: α-interferon (IFN-α), β-interferon (IFN-β), γ-interferon, IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, or TAP2, or functional fragments thereof.

b. Routes of Administration

The vaccine can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The HA antigen can be delivered via DNA injection and along with in vivo electroporation.

c. Electroporation

Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA® EP system (VGX Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

d. Method of Preparing Vaccine

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1 pGX2009 (pH1HA09)—Plasmid Encoding 2009 H1N1 Influenza (Swine Flu) Hemagglutinin Antigen The backbone of pGX2009 (H1 HA09) is the modified expression vector pVAX1 (Invitrogen, Carlsbad, Calif.) under the control of the cytomegalovirus immediate-early (CMV) promoter. The original pVAX1 was purchased from Invitrogen (Catalog number V260-20) and maintained at −20° C. As noted above, sequence analysis revealed differences between the sequence of pVAX1 used as the backbone of pGX2009 and the pVAX1 sequence available from Invitrogen. The differences are set forth above.

Plasmid pGX2009, also referred to as pH1HA09, comprises a nucleic acid sequence that encodes a consensus 2009 H1N1 influenza (swine flu) hemagglutinin molecule. The 79 primary sequences used to generate the consensus sequence were selected from The Influenza Sequence Database.

The accession numbers for nucleotide sequences encoding the amino acid sequence for the various influenza A hemagglutinin H1 proteins as well as the amino acid sequences encoded by the nucleotide sequences are in the GenBank database corresponding to the following accession numbers. The accession numbers not in parentheses disclose nucleotide sequences and additional list amino acid sequences encoded by them. The accession numbers in parentheses are for entries of the corresponding amino acid sequence in GenBank's protein database. The accession numbers are as follows: GQ323579.1 (ACS72657.1), GQ323564.1 (ACS72654.1), GQ323551.1 (ACS72652.1), GQ323530.1 (ACS72651.1), GQ323520.1 (ACS72650.1), GQ323495.1 (ACS72648.1), GQ323489.1 (ACS72647.1), GQ323486.1 (ACS72646.1), GQ323483.1 (ACS72645.1), GQ323455.1 (ACS72641.1), GQ323451.1 (ACS72640.1), GQ323443.1 (ACS72638.1), GQ293077.1 (ACS68822.1), GQ288372.1 (ACS54301.1), GQ287625.1 (ACS54262.1), GQ287627.1 (ACS54263.1), GQ287623.1 (ACS54261.1), GQ287621.1 (ACS54260.1), GQ286175.1 (ACS54258.1), GQ283488.1 (ACS50088.1), GQ280797.1 (ACS45035.1), GQ280624.1 (ACS45017.1), GQ280121.1 (ACS45189.1), GQ261277.1 (ACS34968.1), GQ253498.1 (ACS27787.1), GQ323470.1 (ACS72643.1), GQ253492.1 (ACS27780.1), FJ981613.1 (ACQ55359.1), FJ971076.1 (ACP52565.1), FJ969540.1 (ACP44189.1), FJ969511.1 (ACP44150.1), FJ969509.1 (ACP44147.1), GQ255900.1 (ACS27774.1), GQ255901.1 (ACS27775.1), FJ966974.1 (ACP41953.1), GQ261275.1 (ACS34967.1), FJ966960.1 (ACP41935.1), FJ966952.1 (ACP41926.1), FJ966082.1 (ACP41105.1), GQ255897.1 (ACS27770.1), CY041645.1 (ACS27249.1), CY041637.1 (ACS27239.1), CY041629 (ACS27229.1), GQ323446.1 (ACS72639.1), CY041597.1 (ACS27189.1), CY041581.1 (ACS14726.1), CY040653.1 (ACS14666.1), CY041573.1 (ACS14716.1), CY041565.1 (ACS14706.1), CY041541.1 (ACS14676.1), GQ258462.1 (ACS34667.1), CY041557.1 (ACS14696.1), CY041549.1 (ACS14686.1), GQ283484.1 (ACS50084.1), GQ283493.1 (ACS50095.1), GQ303340.1 (ACS71656.1), GQ287619.1 (ACS54259.1), GQ267839.1 (ACS36632.1), GQ268003.1 (ACS36645.1), CY041621.1 (ACS27219.1), CY041613.1 (ACS27209.1), CY041605.1 (ACS27199.1), FJ966959.1 (ACP41934.1), FJ966982.1 (ACP41963.1), CY039527.2 (ACQ45338.1), FJ981612.1 (ACQ55358.1), FJ981615.1 (ACQ55361.1), FJ982430.1 (ACQ59195.1), FJ998208.1 (ACQ73386.1), GQ259909.1 (ACS34705.1), GQ261272.1 (ACS34966.1), GQ287621.1 (ACS54260.1), GQ290059.1 (ACS66821.1), GQ323464.1 (ACS72642.1), GQ323473.1 (ACS72644.1), GQ323509.1 (ACS72649.1), GQ323560.1 (ACS72653.1), GQ323574.1 (ACS72655.1), and GQ323576.1 (ACS72656.1). The amino acid sequences were downloaded from the NCBI Sequence Database, and an alignment and consensus sequence generated using Clustal X. A highly efficient leader sequence, the IgE leader, was fused in frame upstream of the start codon to facilitate the expression. In order to have a higher level of expression, the codon usage of this fusion gene was adapted to the codon bias of *Homo Sapiens* genes. In addition, RNA optimization was also performed: regions of very high (>80%) or very low (<30%) GC content and the cis-acting sequence motifs such as internal TATA boxes, chi-sites and ribosomal entry sites were avoided. The entire sequence was synthetically produced at Geneart (Regensburg, Germany). The synthetic engineered H1HA09 gene was 1818 bp in length (SEQ ID NO:1) and was cloned into pVAX1 at BamHI and XhoI sites by Geneart (FIG. 2).

Example 2

Challenge of Influenza pGX2009 Immunized Ferrets with A/Mexico/InDRE4487/2009

Challenge experiments were carried out using ferrets, a preferred model for influenza. The ferrets were immunized using plasmid pGX2009.

Animals: 4 groups×5 animals/group, plus one control group with 4 animals=24 ferrets total (male)

Duration: 18 weeks (including challenge)

Dose: 0.2 mg plasmid

Protocol Summary Ferrets were allocated randomly into DNA vaccine groups. Animals were immunized at Study Day 0, Day 28, and Day 56. Animals were anesthetized with ketamine/midazolam cocktail, isoflurane or equivalent according to approved anesthesia protocols and vaccinated IM with influenza DNA vaccine combinations. Groups 1 and 2 were immediately electroporated using CELLECTRA® adaptive constant current electroporation (EP) device at 0.5 Amp, 52 millisecond pulses, 0.2 sec between pulses, 4 sec firing delay, 3 total pulses. Control animals were naïve controls (no plasmid, no EP). Ferrets were allowed to recover from anesthesia in their cages and were closely monitored for 24 hours to ensure full recovery.

Food and water was available ad libitum for the length of the study. On Day 84, animals were challenged by intranasal infection with 1 ml of MX10 (A/Mexico/InDRE4487/2009; 5×105 PFU/ml). Animals were monitored daily for clinical signs (weight, temperature, etc.), using an established and approved scoring sheet. On 1, 3, 6, 9 and 15 dpi nasal washes and rectal swabs were collected. Lungs were collected at day 15. Samples were stored in RNAlater for virus load by real-time PCR, medium for infectious virus (TCDI50) and formalin for histology when appropriated.

FIG. 4 shows a Hemagglutination Inhibition assay performed with sera from immunized ferrets (3 immunizations). A titer of >1:40 is considered "protective". A dotted line indicates the 1:40 mark. All animals were above the 1:40 mark after 3 immunizations. FIG. 5 shows results of a challenge of immunized and unimmunized ferrets with a novel H1N1 strain MX10 (A/Mexico/InDRE4487/2009). All immunized ferrets survived, while 75% of the naive ferrets died within the 15 day period.

The invention claimed is:

1. An isolated nucleic acid molecule comprising one or more nucleic acid sequences selected from the group consisting of:

i) a nucleic acid sequence selected from the group consisting of: SEQ ID NO:1, a nucleic acid sequence that is 95% identical to SEQ ID NO:1; a fragment of SEQ ID NO:1 comprising at least 240 nucleotides, and a nucleic acid sequence that is 99% identical to a fragment of SEQ ID NO:1 comprising at least 240 nucleotides;

ii) a nucleic acid sequence is selected from the group consisting of: SEQ ID NO:3, a nucleic acid sequence that is 95% identical to SEQ ID NO:3; a fragment of SEQ ID NO:3 comprising at least 60 nucleotides, and a nucleic acid sequence that is 95% identical to a fragment of SEQ ID NO:3 comprising at least 60 nucleotides;

iii) a nucleic acid sequence selected from the group consisting of: SEQ ID NO:6, a nucleic acid sequence that is 95% identical to SEQ ID NO:6; a fragment of SEQ ID NO:6 comprising at least 60 nucleotides, and a nucleic acid sequence that is 95% identical to a fragment of SEQ ID NO:6 comprising at least 60 nucleotides;

iv) a nucleic acid sequence selected from the group consisting of: SEQ ID NO:9, a nucleic acid sequence that is 95% identical to SEQ ID NO:9; a fragment of SEQ ID NO:9 comprising at least 60 nucleotides, and a nucleic acid sequence that is 95% identical to a fragment of SEQ ID NO:9 comprising at least 60 nucleotides;

v) a nucleic acid sequence selected from the group consisting of: SEQ ID NO:11, a nucleic acid sequence that is 95% identical to SEQ ID NO:11; a fragment of SEQ ID NO:11 comprising at least 60 nucleotides, and a nucleic acid sequence that is 95% identical to a fragment of SEQ ID NO:11 comprising at least 60 nucleotides.

2. The isolated nucleic acid molecule of claim 1 comprising a nucleic acid sequence selected from the group consisting of: SEQ ID NO:1, SEQ ID NO:3, SEQ ID NO:6, SEQ ID NO:9, and SEQ ID NO:11.

3. The isolated nucleic acid molecule of claim 1 comprising a nucleic acid sequence selected from the group consisting of: a nucleic acid sequence that is 95% identical to SEQ ID NO:1, a nucleic acid sequence that is 95% identical to SEQ ID NO:3, a nucleic acid sequence that is 95% identical to SEQ ID NO:6, a nucleic acid sequence that is 95% identical to SEQ ID NO:9, and a nucleic acid sequence that is 95% identical to SEQ ID NO:11.

4. The isolated nucleic acid molecule of claim 1 comprising a nucleic acid sequence selected from the group consisting of SEQ ID NO:1, SEQ ID NO:6, and SEQ ID NO:9.

5. An expression vector comprising a nucleic acid sequence of claim 1 operably linked to regulatory elements.

6. The expression vector of claim 5 wherein said expression vector is a plasmid.

7. A composition comprising a) a plurality of one or more nucleic acid molecules comprising one or more nucleic acid sequences selected from the group consisting of:

i) a nucleic acid selected from the group consisting of: SEQ ID NO:1, a nucleic acid sequence that is 95% identical to SEQ ID NO:1; a fragment of SEQ ID NO:1 comprising at least 240 nucleotides, and a nucleic acid sequence that is 99% identical to a fragment of SEQ ID NO: 1 comprising at least 240 nucleotides;

ii) a nucleic acid sequence is selected from the group consisting of: SEQ ID NO:3, a nucleic acid sequence that is 95% identical to SEQ ID NO:3; a fragment of SEQ ID NO:3 comprising at least 60 nucleotides, and a nucleic acid sequence that is 95% identical to a fragment of SEQ ID NO:3 comprising at least 60 nucleotides;

iii) a nucleic acid sequence is selected from the group consisting of: SEQ ID NO:6, a nucleic acid sequence that is 95% identical to SEQ ID NO:6; a fragment of SEQ ID NO:6 comprising at least 60 nucleotides, and a nucleic acid sequence that is 95% identical to a fragment of SEQ ID NO:6 comprising at least 60 nucleotides;

iv) a nucleic acid sequence is selected from the group consisting of: SEQ ID NO:9, a nucleic acid sequence that is 95% identical to SEQ ID NO:9; a fragment of SEQ ID NO:9 comprising at least 60 nucleotides, and a nucleic acid sequence that is 95% identical to a fragment of SEQ ID NO:9 comprising at least 60 nucleotides;

v) a nucleic acid sequence is selected from the group consisting of: SEQ ID NO:11, a nucleic acid sequence that is 95% identical to SEQ ID NO:11; a fragment of SEQ ID NO:11 comprising at least 60 nucleotides, and a nucleic acid sequence that is 95% identical to a fragment of SEQ ID NO:11 comprising at least 60 nucleotides; and b) one or more additional nucleic acid sequences that encode one or more proteins selected from the group consisting of one or more of: an influenza A hemagglutinin H1, an influenza A hemagglutinin H2, an influenza A hemagglutinin H3, influenza A hemagglutinin H4, influenza A hemagglutinin H5, influenza A hemagglutinin H6, an influenza A hemagglutinin H7, an influenza A hemagglutinin H8, an influenza A hemagglutinin H9, an influenza A hemagglutinin H10, an influenza A hemagglutinin H11, an influenza A hemagglutinin H12, influenza A hemagglutinin H13, influenza A hemagglutinin H14, an influenza A hemagglutinin H15, influenza A hemagglutinin H16, an influenza A neuraminidase N1, an influenza A neuraminidase N2, an influenza A neuraminidase N3, an influenza A neuraminidase N4, an influenza A neuraminidase N5, an influenza A neuraminidase N6, an influenza A neuraminidase N7, an influenza A neuraminidase N8, an influenza A neuraminidase N9, an influenza B hemagglutinin and an influenza B neuraminidase.

8. The composition of claim 7 wherein said one or more additional nucleic acid sequences are on a plurality of one or more different nucleic acid molecules from the plurality of nucleic acid molecules set forth in section a).

9. The composition of claim 7 wherein the plurality of nucleic acid molecules set forth in section a) comprises one or more nucleic acid sequences selected from the group consisting of: SEQ ID NO:1, SEQ ID NO:3, SEQ ID NO:6, SEQ ID NO:9, and SEQ ID NO:11.

10. The composition of claim 7 wherein the plurality of nucleic acid molecules set forth in section a) comprises one or more nucleic acid sequences selected from the group consisting of: a nucleic acid sequence that is 95% identical to SEQ ID NO:1, a nucleic acid sequence that is 95% identical to SEQ ID NO:3, a nucleic acid sequence that is 95% identical to SEQ ID NO:6, a nucleic acid sequence that is 95% identical to SEQ ID NO:9, and a nucleic acid sequence that is 95% identical to SEQ ID NO:11.

11. The composition of claim 7 wherein the nucleic acid sequences set forth in a) and b) are each operably linked to regulatory elements.

12. The composition of claim 7 wherein the nucleic acid sequences set forth in a) and b) are each operably linked to regulatory elements that are functional in a human cell.

13. The composition of claim 7 wherein the nucleic acid sequences set forth in a) and b) are part of one or more expression vectors.

14. The composition of claim 7 wherein the one or more expression vectors are plasmids.

15. The composition of claim 7 comprising pGX2009 and/or pGX2006.

16. The composition of claim 7 comprising one or more of:

a nucleic acid sequence comprising SEQ ID NO:1;

a nucleic acid sequence comprising SEQ ID NO:6;

a nucleic acid sequence comprising SEQ ID NO:9;

a nucleic acid sequence comprising SEQ ID NO:13;

a nucleic acid sequence that encodes an influenza A hemagglutinin H1;

and a nucleic acid sequence that encodes an influenza A hemagglutinin H3.

17. The composition of claim 7, wherein the one or more additional nucleic acids encode an influenza A hemagglutinin H1 comprising SEQ ID NO:19 and an influenza A hemagglutinin H3 comprising SEQ ID NO:20.

18. The composition of claim 16 comprising:

a nucleic acid molecule comprising SEQ ID NO:9;

a nucleic acid molecule comprising SEQ ID NO:13; and a nucleic acid molecule that encodes an influenza A hemagglutinin H3 comprising SEQ ID NO:20.

19. The composition of claim 18 wherein the nucleic acid molecule comprising SEQ ID NO:9 is a plasmid;

the nucleic acid molecule comprising SEQ ID NO:13 is a plasmid; and the nucleic acid molecule that encodes an influenza A hemagglutinin H3 comprising SEQ ID NO:20 is a plasmid.

* * * * *

SEQUENCE LISTING

<160> NUMBER OF SEQ ID NOS: 20

<210> SEQ ID NO 1
<211> LENGTH: 1695
<212> TYPE: DNA
<213> ORGANISM: Artificial Sequence
<220> FEATURE:
<223> OTHER INFORMATION: Influenza H1 DNA sequence

<400> SEQUENCE: 1

```
atgaaggcta tcctcgtcgt gctgctgtac accttcgcca ccgccaacgc cgataccctg     60
tgcatcggct accacgccaa caacagcacc gacaccgtgg ataccgtgct ggaaaagaac    120
gtgaccgtga cccacagcgt gaacctgctg gaagataagc acaacggcaa gctgtgcaag    180
ctgagaggcg tggcccctct gcacctgggc aagtgcaata tcgccggctg gattctgggc    240
aaccccgagt gcgagagcct gtctaccgct agctcctggt cctacatcgt ggagacaagc    300
agcagcgaca acggcacctg ttaccccggc gacttcatcg actacgagga actgcgggag    360
cagctgagca gcgtgtccag cttcgagcgg ttcgagatct tccccaagac cagctcctgg    420
cccaaccacg acagcaacaa gggcgtgacc gccgcctgtc ctcacgctgg cgccaagagc    480
ttctacaaga acctgatctg gctggtcaag aagggcaaca gctaccccaa gctgagcaag    540
agctacatca acgacaaggg caaagaggtc ctcgtcctct ggggcatcca ccaccctagc    600
accagcgccg accagcagag cctgtaccag aacgccgacg cctacgtgtt cgtgggctca    660
tctcggtaca gcaagaagtt caagcccgag atcgccatca gacccaaagt gcgggaccag    720
gaaggccgga tgaactacta ctggaccctg gtggagcccg gcgacaagat caccttcgag    780
gccaccggca atctggtggt gcccagatac gccttcgcca tggaaagaaa cgccggcagc    840
ggcatcatca tcagcgacac ccccgtgcac gactgcaaca ccacctgtca gacccccaag    900
ggcgccatca acaccagcct gcccttccag aacatccacc ccatcaccat cggcaagtgc    960
cctaagtacg tgaagtccac taagctcaga ctggccaccg gcctgagaaa cgtgcccagc   1020
atccagagca gaggcctgtt tggcgccatt gccggcttta tcgagggcgg ctggaccgga   1080
atggtggacg ggtggtacgg ctaccaccac cagaatgagc agggcagcgg ctacgccgcc   1140
gacctgaagt ccacacagaa cgccatcgac gagatcacca acaaagtgaa cagcgtgatc   1200
gagaagatga acacccagtt caccgccgtg ggcaaagagt tcaaccacct ggaaaagcgg   1260
atcgagaacc tgaacaagaa ggtggacgac ggcttcctgg acatctggac ctacaacgcc   1320
gagctgctgg tgctgctgga aaacgagcgg accctggact accacgactc caacgtgaag   1380
aatctgtacg agaaagtgcg gagccagctg aagaacaacg ccaaagagat cggcaacggc   1440
tgcttcgagt tctaccacaa gtgcgacaac acctgtatgg aaagcgtgaa gaacggcacc   1500
tacgactacc ccaagtacag cgaggaagcc aagctgaacc gggaagagat cgacggcgtg   1560
aagctggaaa gcacccggat ctaccagatc ctggccatct actctactgt ggccagctca   1620
ctggtgctgg tggtgtccct gggcgccatc tcctttttgga tgtgctccaa cggcagcctg   1680
```

-continued

```
cagtgccgga tctgc                                                      1695


<210> SEQ ID NO 2
<211> LENGTH: 566
<212> TYPE: PRT
<213> ORGANISM: Artificial Sequence
<220> FEATURE:
<223> OTHER INFORMATION: Influenza Protein H1 Sequence

<400> SEQUENCE: 2

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
```

```
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 3
<211> LENGTH: 1818
<212> TYPE: DNA
<213> ORGANISM: Artificial Sequence
<220> FEATURE:
<223> OTHER INFORMATION: IgE-H1-HAT Antigen DNA Sequence

<400> SEQUENCE: 3

ttaattaagg atccgccacc atggactgga cctggattct gttcctggtg gctgctgcca     60

ctagagtgca cagcatgaag gctatcctcg tcgtgctgct gtacaccttc gccaccgcca    120

acgccgatac cctgtgcatc ggctaccacg ccaacaacag caccgacacc gtggataccg    180

tgctggaaaa gaacgtgacc gtgacccaca gcgtgaacct gctggaagat aagcacaacg    240

gcaagctgtg caagctgaga ggcgtggccc ctctgcacct gggcaagtgc aatatcgccg    300

gctggattct gggcaacccc gagtgcgaga gcctgtctac cgctagctcc tggtcctaca    360

tcgtggagac aagcagcagc gacaacggca cctgttaccc cggcgacttc atcgactacg    420

aggaactgcg ggagcagctg agcagcgtgt ccagcttcga gcggttcgag atcttcccca    480

agaccagctc ctggcccaac cacgacagca acaagggcgt gaccgccgcc tgtcctcacg    540

ctggcgccaa gagcttctac aagaacctga tctggctggt caagaagggc aacagctacc    600

ccaagctgag caagagctac atcaacgaca agggcaaaga ggtcctcgtc ctctggggca    660

tccaccaccc tagcaccagc gccgaccagc agagcctgta ccagaacgcc gacgcctacg    720

tgttcgtggg ctcatctcgg tacagcaaga agttcaagcc cgagatcgcc atcagaccca    780

aagtgcggga ccaggaaggc cggatgaact actactggac cctggtggag cccggcgaca    840
```

-continued

```
agatcacctt cgaggccacc ggcaatctgg tggtgcccag atacgccttc gccatggaaa    900

gaaacgccgg cagcggcatc atcatcagcg acaccccgt gcacgactgc aacaccacct     960

gtcagacccc caagggcgcc atcaacacca gcctgccctt ccagaacatc caccccatca   1020

ccatcggcaa gtgccctaag tacgtgaagt ccactaagct cagactggcc accggcctga   1080

gaaacgtgcc cagcatccag agcagaggcc tgtttggcgc cattgccggc tttatcgagg   1140

gcggctggac cggaatggtg gacgggtggt acggctacca ccaccagaat gagcagggca   1200

gcggctacgc cgccgacctg aagtccacac agaacgccat cgacgagatc accaacaaag   1260

tgaacagcgt gatcgagaag atgaacaccc agttcaccgc cgtgggcaaa gagttcaacc   1320

acctggaaaa gcggatcgag aacctgaaca agaaggtgga cgacggcttc ctggacatct   1380

ggacctacaa cgccgagctg ctggtgctgc tggaaaacga gcggaccctg gactaccacg   1440

actccaacgt gaagaatctg tacgagaaag tgcggagcca gctgaagaac aacgccaaag   1500

agatcggcaa cggctgcttc gagttctacc acaagtgcga caacacctgt atggaaagcg   1560

tgaagaacgg cacctacgac taccccaagt acagcgagga agccaagctg aaccgggaag   1620

agatcgacgg cgtgaagctg gaaagcaccc ggatctacca gatcctggcc atctactcta   1680

ctgtggccag ctcactggtg ctggtggtgt ccctgggcgc catctccttt tggatgtgct   1740

ccaacggcag cctgcagtgc cggatctgca tctacccccta cgacgtgccc gactacgcct  1800

gatgactcga ggcgcgcc                                                 1818
```

```
<210> SEQ ID NO 4
<211> LENGTH: 593
<212> TYPE: PRT
<213> ORGANISM: Artificial Sequence
<220> FEATURE:
<223> OTHER INFORMATION: IgE-H1-HATanitgen amino acid seqeunce

<400> SEQUENCE: 4

Met Asp Trp Thr Trp Ile Leu Phe Leu Val Ala Ala Ala Thr Arg Val
1               5                   10                  15

His Ser Met Lys Ala Ile Leu Val Val Leu Leu Tyr Thr Phe Ala Thr
            20                  25                  30

Ala Asn Ala Asp Thr Leu Cys Ile Gly Tyr His Ala Asn Asn Ser Thr
        35                  40                  45

Asp Thr Val Asp Thr Val Leu Glu Lys Asn Val Thr Val Thr His Ser
    50                  55                  60

Val Asn Leu Leu Glu Asp Lys His Asn Gly Lys Leu Cys Lys Leu Arg
65                  70                  75                  80

Gly Val Ala Pro Leu His Leu Gly Lys Cys Asn Ile Ala Gly Trp Ile
                85                  90                  95

Leu Gly Asn Pro Glu Cys Glu Ser Leu Ser Thr Ala Ser Ser Trp Ser
            100                 105                 110

Tyr Ile Val Glu Thr Ser Ser Ser Asp Asn Gly Thr Cys Tyr Pro Gly
        115                 120                 125

Asp Phe Ile Asp Tyr Glu Glu Leu Arg Glu Gln Leu Ser Ser Val Ser
    130                 135                 140

Ser Phe Glu Arg Phe Glu Ile Phe Pro Lys Thr Ser Ser Trp Pro Asn
145                 150                 155                 160

His Asp Ser Asn Lys Gly Val Thr Ala Ala Cys Pro His Ala Gly Ala
                165                 170                 175

Lys Ser Phe Tyr Lys Asn Leu Ile Trp Leu Val Lys Lys Gly Asn Ser
            180                 185                 190
```

-continued

```
Tyr Pro Lys Leu Ser Lys Ser Tyr Ile Asn Asp Lys Gly Lys Glu Val
        195                 200                 205

Leu Val Leu Trp Gly Ile His His Pro Ser Thr Ser Ala Asp Gln Gln
    210                 215                 220

Ser Leu Tyr Gln Asn Ala Asp Ala Tyr Val Phe Val Gly Ser Ser Arg
225                 230                 235                 240

Tyr Ser Lys Lys Phe Lys Pro Glu Ile Ala Ile Arg Pro Lys Val Arg
                245                 250                 255

Asp Gln Glu Gly Arg Met Asn Tyr Tyr Trp Thr Leu Val Glu Pro Gly
            260                 265                 270

Asp Lys Ile Thr Phe Glu Ala Thr Gly Asn Leu Val Val Pro Arg Tyr
        275                 280                 285

Ala Phe Ala Met Glu Arg Asn Ala Gly Ser Gly Ile Ile Ile Ser Asp
    290                 295                 300

Thr Pro Val His Asp Cys Asn Thr Thr Cys Gln Thr Pro Lys Gly Ala
305                 310                 315                 320

Ile Asn Thr Ser Leu Pro Phe Gln Asn Ile His Pro Ile Thr Ile Gly
                325                 330                 335

Lys Cys Pro Lys Tyr Val Lys Ser Thr Lys Leu Arg Leu Ala Thr Gly
            340                 345                 350

Leu Arg Asn Val Pro Ser Ile Gln Ser Arg Gly Leu Phe Gly Ala Ile
        355                 360                 365

Ala Gly Phe Ile Glu Gly Gly Trp Thr Gly Met Val Asp Gly Trp Tyr
    370                 375                 380

Gly Tyr His His Gln Asn Glu Gln Gly Ser Gly Tyr Ala Ala Asp Leu
385                 390                 395                 400

Lys Ser Thr Gln Asn Ala Ile Asp Glu Ile Thr Asn Lys Val Asn Ser
                405                 410                 415

Val Ile Glu Lys Met Asn Thr Gln Phe Thr Ala Val Gly Lys Glu Phe
            420                 425                 430

Asn His Leu Glu Lys Arg Ile Glu Asn Leu Asn Lys Lys Val Asp Asp
        435                 440                 445

Gly Phe Leu Asp Ile Trp Thr Tyr Asn Ala Glu Leu Leu Val Leu Leu
    450                 455                 460

Glu Asn Glu Arg Thr Leu Asp Tyr His Asp Ser Asn Val Lys Asn Leu
465                 470                 475                 480

Tyr Glu Lys Val Arg Ser Gln Leu Lys Asn Asn Ala Lys Glu Ile Gly
                485                 490                 495

Asn Gly Cys Phe Glu Phe Tyr His Lys Cys Asp Asn Thr Cys Met Glu
            500                 505                 510

Ser Val Lys Asn Gly Thr Tyr Asp Tyr Pro Lys Tyr Ser Glu Glu Ala
        515                 520                 525

Lys Leu Asn Arg Glu Glu Ile Asp Gly Val Lys Leu Glu Ser Thr Arg
    530                 535                 540

Ile Tyr Gln Ile Leu Ala Ile Tyr Ser Thr Val Ala Ser Ser Leu Val
545                 550                 555                 560

Leu Val Val Ser Leu Gly Ala Ile Ser Phe Trp Met Cys Ser Asn Gly
                565                 570                 575

Ser Leu Gln Cys Arg Ile Cys Ile Tyr Pro Tyr Asp Val Pro Asp Tyr
            580                 585                 590

Ala
```

-continued

<210> SEQ ID NO 5
<211> LENGTH: 4739
<212> TYPE: DNA
<213> ORGANISM: Artificial Sequence
<220> FEATURE:
<223> OTHER INFORMATION: pGX2009

<400> SEQUENCE: 5
gctgcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
gtatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttggt 720
accgagctcg gatccgccac catggactgg acctggattc tgttcctggt ggctgctgcc 780
actagagtgc acagcatgaa ggctatcctc gtcgtgctgc tgtacacctt cgccaccgcc 840
aacgccgata ccctgtgcat cggctaccac gccaacaaca gcaccgacac cgtggatacc 900
gtgctggaaa agaacgtgac cgtgacccac agcgtgaacc tgctggaaga taagcacaac 960
ggcaagctgt gcaagctgag aggcgtggcc cctctgcacc tgggcaagtg caatatcgcc 1020
ggctggattc tgggcaaccc cgagtgcgag agcctgtcta ccgctagctc ctggtcctac 1080
atcgtggaga caagcagcag cgacaacggc acctgttacc ccggcgactt catcgactac 1140
gaggaactgc gggagcagct gagcagcgtg tccagcttcg agcggttcga gatcttcccc 1200
aagaccagct cctggcccaa ccacgacagc aacaagggcg tgaccgccgc ctgtcctcac 1260
gctggcgcca agagcttcta caagaacctg atctggctgg tcaagaaggg caacagctac 1320
cccaagctga gcaagagcta catcaacgac aagggcaaag aggtcctcgt cctctggggc 1380
atccaccacc ctagcaccag cgccgaccag cagagcctgt accagaacgc cgacgcctac 1440
gtgttcgtgg gctcatctcg gtacagcaag aagttcaagc ccgagatcgc catcagaccc 1500
aaagtgcggg accaggaagg ccggatgaac tactactgga ccctggtgga gcccggcgac 1560
aagatcacct tcgaggccac cggcaatctg gtggtgccca gatacgcctt cgccatggaa 1620
agaaacgccg gcagcggcat catcatcagc gacacccccg tgcacgactg caacaccacc 1680
tgtcagaccc ccaagggcgc catcaacacc agcctgccct tccagaacat ccaccccatc 1740
accatcggca agtgccctaa gtacgtgaag tccactaagc tcagactggc caccggcctg 1800
agaaacgtgc ccagcatcca gagcagaggc ctgtttggcg ccattgccgg ctttatcgag 1860
ggcggctgga ccggaatggt ggacgggtgg tacggctacc accaccagaa tgagcagggc 1920
agcggctacg ccgccgacct gaagtccaca cagaacgcca tcgacgagat caccaacaaa 1980
gtgaacagcg tgatcgagaa gatgaacacc cagttcaccg ccgtgggcaa agagttcaac 2040
cacctggaaa agcggatcga gaacctgaac aagaaggtgg acgacggctt cctggacatc 2100

-continued

```
tggacctaca acgccgagct gctggtgctg ctggaaaacg agcggaccct ggactaccac   2160
gactccaacg tgaagaatct gtacgagaaa gtgcggagcc agctgaagaa caacgccaaa   2220
gagatcggca acggctgctt cgagttctac cacaagtgcg acaacacctg tatggaaagc   2280
gtgaagaacg gcacctacga ctaccccaag tacagcgagg aagccaagct gaaccgggaa   2340
gagatcgacg gcgtgaagct ggaaagcacc cggatctacc agatcctggc catctactct   2400
actgtggcca gctcactggt gctggtggtg tccctgggcg ccatctcctt ttggatgtgc   2460
tccaacggca gcctgcagtg ccggatctgc atctacccct acgacgtgcc cgactacgcc   2520
tgatgactcg agtctagagg gcccgtttaa acccgctgat cagcctcgac tgtgccttct   2580
agttgccagc catctgttgt ttgcccctcc cccgtgcctt ccttgaccct ggaaggtgcc   2640
actcccactg tcctttccta ataaaatgag gaaattgcat cgcattgtct gagtaggtgt   2700
cattctattc tggggggtgg ggtggggcag gacagcaagg gggaggattg ggaagacaat   2760
agcaggcatg ctggggatgc ggtgggctct atggcttcta ctgggcggtt ttatggacag   2820
caagcgaacc ggaattgcca gctggggcgc cctctggtaa ggttgggaag ccctgcaaag   2880
taaactggat ggctttcttg ccgccaagga tctgatggcg caggggatca agctctgatc   2940
aagagacagg atgaggatcg tttcgcatga ttgaacaaga tggattgcac gcaggttctc   3000
cggccgcttg ggtggagagg ctattcggct atgactgggc acaacagaca atcggctgct   3060
ctgatgccgc cgtgttccgg ctgtcagcgc aggggcgccc ggttcttttt gtcaagaccg   3120
acctgtccgg tgccctgaat gaactgcaag acgaggcagc gcggctatcg tggctggcca   3180
cgacgggcgt tccttgcgca gctgtgctcg acgttgtcac tgaagcggga agggactggc   3240
tgctattggg cgaagtgccg gggcaggatc tcctgtcatc tcaccttgct cctgccgaga   3300
aagtatccat catggctgat gcaatgcggc ggctgcatac gcttgatccg gctacctgcc   3360
cattcgacca ccaagcgaaa catcgcatcg agcgagcacg tactcggatg gaagccggtc   3420
ttgtcgatca ggatgatctg gacgaagagc atcaggggct cgcgccagcc gaactgttcg   3480
ccaggctcaa ggcgagcatg cccgacggcg aggatctcgt cgtgacccat ggcgatgcct   3540
gcttgccgaa tatcatggtg gaaaatggcc gcttttctgg attcatcgac tgtggccggc   3600
tgggtgtggc ggaccgctat caggacatag cgttggctac ccgtgatatt gctgaagagc   3660
ttggcggcga atgggctgac cgcttcctcg tgctttacgg tatcgccgct cccgattcgc   3720
agcgcatcgc cttctatcgc cttcttgacg agttcttctg aattattaac gcttacaatt   3780
tcctgatgcg gtattttctc cttacgcatc tgtgcggtat ttcacaccgc atcaggtggc   3840
acttttcggg gaaatgtgcg cggaacccct atttgtttat ttttctaaat acattcaaat   3900
atgtatccgc tcatgagaca ataaccctga taaatgcttc aataatagca cgtgctaaaa   3960
cttcattttt aatttaaaag gatctaggtg aagatccttt ttgataatct catgaccaaa   4020
atcccttaac gtgagttttc gttccactga gcgtcagacc ccgtagaaaa gatcaaagga   4080
tcttcttgag atcctttttt tctgcgcgta atctgctgct tgcaaacaaa aaaaccaccg   4140
ctaccagcgg tggtttgttt gccggatcaa gagctaccaa ctctttttcc gaaggtaact   4200
ggcttcagca gagcgcagat accaaatact gttcttctag tgtagccgta gttaggccac   4260
cacttcaaga actctgtagc accgcctaca tacctcgctc tgctaatcct gttaccagtg   4320
gctgctgcca gtggcgataa gtcgtgtctt accgggttgg actcaagacg atagttaccg   4380
gataaggcgc agcggtcggg ctgaacgggg ggttcgtgca cacagcccag cttggagcga   4440
acgacctaca ccgaactgag atacctacag cgtgagctat gagaaagcgc cacgcttccc   4500
```

-continued gaagggagaa aggcggacag gtatccggta agcggcaggg tcggaacagg agagcgcacg 4560
agggagcttc caggggggaaa cgcctggtat ctttatagtc ctgtcgggtt tcgccacctc 4620
tgacttgagc gtcgattttt gtgatgctcg tcaggggggc ggagcctatg gaaaaacgcc 4680
agcaacgcgg cctttttacg gttcctggcc ttttgctggc cttttgctca catgttctt 4739

<210> SEQ ID NO 6
<211> LENGTH: 1719
<212> TYPE: DNA
<213> ORGANISM: Artificial Sequence
<220> FEATURE:
<223> OTHER INFORMATION: Influenza H2 antigen DNA sequence

<400> SEQUENCE: 6
ggtaccaagc ttgccaccat ggccatcatc tacctgatcc tgctgttcac cgccgtgcgg 60
ggcgaccaga tctgcatcgg ctaccacgcc aacaacagca ccgagaaggt ggacaccatc 120
ctggaacgga acgtgaccgt gacccacgcc aaggacatcc tggaaaagac ccacaacggc 180
aagctgtgca agctgaacgg catccccccc ctggaactgg gcgactgcag cattgccggc 240
tggctgctgg gcaaccccga gtgcgaccgg ctgctgtccg tgcccgagtg gagctacatc 300
atggaaaaag agaacccccg ggacggcctg tgctaccccg gcagcttcaa cgactacgag 360
gaactgaagc acctgctgtc cagcgtgaag cacttcgaga aggtgaaaat cctgcccaag 420
gaccggtgga cccagcacac caccaccggc ggcagcagag cctgtgccgt gagcggcaac 480
cccagcttct tccggaacat ggtgtggctg accaagaagg gcagcaacta ccccgtggcc 540
aagggcagct acaacaacac ctccggagaa cagatgctga tcatctgggg cgtgcaccac 600
cccaacgacg agacagagca gcggaccctg taccagaacg tgggcaccta cgtgagcgtg 660
ggcaccagca ccctgaacaa gcggagcacc cccgagatcg ccacccggcc caaggtgaac 720
ggcctgggca gccggatgga attcagctgg accctgctgg acatgtggga caccatcaac 780
ttcgagagca ccggcaacct gatcgccccc gagtacggct tcaagatcag caagcggggc 840
agcagcggca tcatgaaaac cgagggcacc ctggaaaact gcgagacaaa gtgccagacc 900
cccctgggcg ccatcaacac caccctgccc ttccacaacg tgcacccccct gaccatcggc 960 gagtgcccca agtacgtgaa gagcgagaag ctggtgctgg ccaccggcct gcggaacgtg 1020
ccccagatcg agagcagggg cctgttcggc gccattgccg gattcatcga gggcggctgg 1080
cagggcatgg tggacgggtg gtacggctac caccacagca acgaccaggg cagcggctac 1140
gccgccgaca aagagagcac ccagaaggcc ttcgacggca tcaccaacaa ggtgaacagc 1200
gtgatcgaga agatgaacac ccagttcgag gccgtgggca aagagttcag caacctggaa 1260
cggcggctgg aaaacctgaa caagaaaatg gaagatggct tcctggacgt gtggacctac 1320
aacgccgagc tgctggtgct gatggaaaac gagaggaccc tggacttcca cgacagcaac 1380
gtgaagaacc tgtacgacaa agtgcggatg cagctgcggg acaacgtgaa agagctgggc 1440
aacggctgct tcgagttcta ccacaagtgc gacgacgagt gcatgaactc cgtgaagaac 1500
ggcacctacg actaccctaa gtacgaggaa gagtccaagc tgaaccggaa cgagatcaag 1560
ggcgtgaagc tgtccagcat gggcgtgtac cagatcctgg ccatctacgc caccgtggcc 1620
ggcagcctga gcctggctat tatgatggct ggcatcagct tttggatgtg cagcaacggc 1680
agcctgcagt gccggatctg catctgatga ctcgagctc 1719

<210> SEQ ID NO 7

<211> LENGTH: 562
<212> TYPE: PRT
<213> ORGANISM: Artificial Sequence
<220> FEATURE:
<223> OTHER INFORMATION: Influenza H2 amino acid sequence

<400> SEQUENCE: 7

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380
```

-continued

Phe Asp Gly Ile Thr Asn Lys Val Asn Ser Val Ile Glu Lys Met Asn
385 390 395 400

Thr Gln Phe Glu Ala Val Gly Lys Glu Phe Ser Asn Leu Glu Arg Arg
405 410 415

Leu Glu Asn Leu Asn Lys Lys Met Glu Asp Gly Phe Leu Asp Val Trp
420 425 430

Thr Tyr Asn Ala Glu Leu Leu Val Leu Met Glu Asn Glu Arg Thr Leu
435 440 445

Asp Phe His Asp Ser Asn Val Lys Asn Leu Tyr Asp Lys Val Arg Met
450 455 460

Gln Leu Arg Asp Asn Val Lys Glu Leu Gly Asn Gly Cys Phe Glu Phe
465 470 475 480

Tyr His Lys Cys Asp Asp Glu Cys Met Asn Ser Val Lys Asn Gly Thr
485 490 495

Tyr Asp Tyr Pro Lys Tyr Glu Glu Glu Ser Lys Leu Asn Arg Asn Glu
500 505 510

Ile Lys Gly Val Lys Leu Ser Ser Met Gly Val Tyr Gln Ile Leu Ala
515 520 525

Ile Tyr Ala Thr Val Ala Gly Ser Leu Ser Leu Ala Ile Met Met Ala
530 535 540

Gly Ile Ser Phe Trp Met Cys Ser Asn Gly Ser Leu Gln Cys Arg Ile
545 550 555 560

Cys Ile

<210> SEQ ID NO 8
<211> LENGTH: 4628
<212> TYPE: DNA
<213> ORGANISM: Artificial Sequence
<220> FEATURE:
<223> OTHER INFORMATION: pGX2006 DNA sequence

<400> SEQUENCE: 8
gactcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
gtatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttgcc 720
accatggcca tcatctacct gatcctgctg ttcaccgccg tgcggggcga ccagatctgc 780
atcggctacc acgccaacaa cagcaccgag aaggtggaca ccatcctgga acggaacgtg 840
accgtgaccc acgccaagga catcctggaa aagacccaca acggcaagct gtgcaagctg 900
aacggcatcc ccccccctgga actgggcgac tgcagcattg ccggctggct gctgggcaac 960
cccgagtgcg accggctgct gtccgtgccc gagtggagct acatcatgga aaaagagaac 1020

-continued

```
ccccgggacg gcctgtgcta ccccggcagc ttcaacgact acgaggaact gaagcacctg   1080
ctgtccagcg tgaagcactt cgagaaggtg aaaatcctgc ccaaggaccg gtggacccag   1140
cacaccacca ccggcggcag cagagcctgt gccgtgagcg gcaaccccag cttcttccgg   1200
aacatggtgt ggctgaccaa gaagggcagc aactaccccg tggccaaggg cagctacaac   1260
aacacctccg gagaacagat gctgatcatc tggggcgtgc accaccccaa cgacgagaca   1320
gagcagcgga ccctgtacca gaacgtgggc acctacgtga gcgtgggcac cagcaccctg   1380
aacaagcgga gcacccccga gatcgccacc cggcccaagg tgaacggcct gggcagccgg   1440
atggaattca gctggaccct gctggacatg tgggacacca tcaacttcga gagcaccggc   1500
aacctgatcg cccccgagta cggcttcaag atcagcaagc ggggcagcag cggcatcatg   1560
aaaaccgagg gcaccctgga aaactgcgag acaaagtgcc agaccccccct gggcgccatc   1620
aacaccaccc tgcccttcca caacgtgcac cccctgacca tcggcgagtg ccccaagtac   1680
gtgaagagcg agaagctggt gctggccacc ggcctgcgga acgtgcccca gatcgagagc   1740
aggggcctgt tcggcgccat tgccggattc atcgagggcg gctggcaggg catggtggac   1800
gggtggtacg gctaccacca cagcaacgac cagggcagcg gctacgccgc cgacaaagag   1860
agcacccaga aggccttcga cggcatcacc aacaaggtga acagcgtgat cgagaagatg   1920
aacacccagt tcgaggccgt gggcaaagag ttcagcaacc tggaacggcg gctggaaaac   1980
ctgaacaaga aaatggaaga tggcttcctg gacgtgtgga cctacaacgc cgagctgctg   2040
gtgctgatgg aaaacgagag gaccctggac ttccacgaca gcaacgtgaa gaacctgtac   2100
gacaaagtgc ggatgcagct gcgggacaac gtgaaagagc tgggcaacgg ctgcttcgag   2160
ttctaccaca agtgcgacga cgagtgcatg aactccgtga agaacggcac ctacgactac   2220
cctaagtacg aggaagagtc caagctgaac cggaacgaga tcaagggcgt gaagctgtcc   2280
agcatgggcg tgtaccagat cctggccatc tacgccaccg tggccggcag cctgagcctg   2340
gctattatga tggctggcat cagcttttgg atgtgcagca acggcagcct gcagtgccgg   2400
atctgcatct gatgactcga gtctagaggg cccgtttaaa cccgctgatc agcctcgact   2460
gtgccttcta gttgccagcc atctgttgtt tgcccctccc ccgtgccttc cttgaccctg   2520
gaaggtgcca ctcccactgt cctttcctaa taaaatgagg aaattgcatc gcattgtctg   2580
agtaggtgtc attctattct ggggggtggg gtggggcagg acagcaaggg ggaggattgg   2640
gaagacaata gcaggcatgc tggggatgcg gtgggctcta tggcttctac tgggcggttt   2700
tatggacagc aagcgaaccg gaattgccag ctggggcgcc ctctggtaag gttgggaagc   2760
cctgcaaagt aaactggatg gctttcttgc cgccaaggat ctgatggcgc aggggatcaa   2820
gctctgatca agagacagga tgaggatcgt ttcgcatgat tgaacaagat ggattgcacg   2880
caggttctcc ggccgcttgg gtggagaggc tattcggcta tgactgggca caacagacaa   2940
tcggctgctc tgatgccgcc gtgttccggc tgtcagcgca ggggcgcccg gttctttttg   3000
tcaagaccga cctgtccggt gccctgaatg aactgcaaga cgaggcagcg cggctatcgt   3060
ggctggccac gacgggcgtt ccttgcgcag ctgtgctcga cgttgtcact gaagcgggaa   3120
gggactggct gctattgggc gaagtgccgg ggcaggatct cctgtcatct caccttgctc   3180
ctgccgagaa agtatccatc atggctgatg caatgcggcg gctgcatacg cttgatccgg   3240
ctacctgccc attcgaccac caagcgaaac atcgcatcga gcgagcacgt actcggatgg   3300
aagccggtct tgtcgatcag gatgatctgg acgaagagca tcaggggctc gcgccagccg   3360
```

-continued

```
aactgttcgc caggctcaag gcgagcatgc ccgacggcga ggatctcgtc gtgacccatg   3420

gcgatgcctg cttgccgaat atcatggtgg aaaatggccg cttttctgga ttcatcgact   3480

gtggccggct gggtgtggcg gaccgctatc aggacatagc gttggctacc cgtgatattg   3540

ctgaagagct tggcggcgaa tgggctgacc gcttcctcgt gctttacggt atcgccgctc   3600

ccgattcgca gcgcatcgcc ttctatcgcc ttcttgacga gttcttctga attattaacg   3660

cttacaattt cctgatgcgg tattttctcc ttacgcatct gtgcggtatt tcacaccgca   3720

tcaggtggca cttttcgggg aaatgtgcgc ggaaccccta tttgtttatt tttctaaata   3780

cattcaaata tgtatccgct catgagacaa taaccctgat aaatgcttca ataatagcac   3840

gtgctaaaac ttcattttta atttaaaagg atctaggtga agatcctttt tgataatctc   3900

atgaccaaaa tcccttaacg tgagttttcg ttccactgag cgtcagaccc cgtagaaaag   3960

atcaaaggat cttcttgaga tccttttttt ctgcgcgtaa tctgctgctt gcaaacaaaa   4020

aaaccaccgc taccagcggt ggtttgtttg ccggatcaag agctaccaac tctttttccg   4080

aaggtaactg gcttcagcag agcgcagata ccaaatactg ttcttctagt gtagccgtag   4140

ttaggccacc acttcaagaa ctctgtagca ccgcctacat acctcgctct gctaatcctg   4200

ttaccagtgg ctgctgccag tggcgataag tcgtgtctta ccgggttgga ctcaagacga   4260

tagttaccgg ataaggcgca gcggtcgggc tgaacggggg gttcgtgcac acagcccagc   4320

ttggagcgaa cgacctacac cgaactgaga tacctacagc gtgagctatg agaaagcgcc   4380

acgcttcccg aagggagaaa ggcggacagg tatccggtaa gcggcagggt cggaacagga   4440

gagcgcacga gggagcttcc agggggaaac gcctggtatc tttatagtcc tgtcgggttt   4500

cgccacctct gacttgagcg tcgatttttg tgatgctcgt caggggggcg gagcctatgg   4560

aaaaacgcca gcaacgcggc ctttttacgg ttcctggcct tttgctggcc ttttgctcac   4620

atgttctt                                                            4628
```

<210> SEQ ID NO 9
<211> LENGTH: 1695
<212> TYPE: DNA
<213> ORGANISM: Artificial Sequence
<220> FEATURE:
<223> OTHER INFORMATION: Influenza U2 DNA sequence

<400> SEQUENCE: 9

```
aaggccaagc tgctggtgct gctgtgcacc ttcgccgcca ccaacgccga caccatctgc     60

atcggctacc acgccaacaa cagcaccgac accgtggata ccgtgctgga aaagaacgtg    120

accgtgaccc acagcgtgaa cctgctggaa gataagcaca acggcaagct gtgcaagctg    180

aagggaatcg ccccccctgca gctgggcaag tgcaatatcg ccggctggat tctgggcaac    240

cccgagtgcg agagcctgag cagcaagagc agctggtcct acatcgtgga aacccccaac    300

agcgagaacg gcacctgtta ccccggcgac ttcgccgact acgaggaact gcgcgagcag    360

ctgagcagcg tgtccagctt cgagagattc gagatcttcc ccaagaccag cagctggccc    420

aaccacgacg tgaccaaggg cgtgaccgct agctgtagcc acgcaggcgc cagcagcttc    480

tacaagaacc tgctgtggct gaccaagaag aacggcagct accccaagct gagcaagagc    540

tacatcaaca acaaagaaaa agaggtgctg gtcctctggg gcgtccacca ccccagcaca    600

atcgccgacc agcagagcct gtaccagaac gagaacgcct acgtgtccgt gggcagcagc    660

cactacagcc ggaagttcac ccccgagatc gccaagcggc ccaaagtgcg ggaccaggaa    720

ggccggatca actactactg gaccctgctg gaacccggcg acaccatcat cttcgaggcc    780
```

```
aacggcaacc tgatcgcccc cagatacgcc ttcgccctga gcagaggctt cggcagcggc    840

atcatcatca gcaacgcccc catgcacgac tgcgacacca agtgccagac ccctcagggc    900

gccatcaaca gcagcctgcc cttccagaac atccaccccg tgaccatcgg cgagtgcccc    960

aaatacgtgc ggagcaccaa gctgcggatg gccaccggcc tgcggaacat ccccagcatc   1020

cagagcagag gcctgttcgg cgccattgcc ggcttcatcg agggcggctg gaccggaatg   1080

gtggacgggt ggtacggcta ccaccaccag aatgagcagg gcagcggcta cgccgccgac   1140

cagaagtcca cccagaacgc catcgacggc atcaccaaca aagtgaacag cgtgatcgag   1200

aagatgaaca cccagttcac cgccgtgggc aaagagttca acaagctgga aaagcggatg   1260

gaaaacctga acaagaaggt ggacgacggc ttcctggaca tctggaccta caacgccgaa   1320

ctgctcgtgc tgctggaaaa cgagcggacc ctggacttcc acgacagcaa cgtgaagaac   1380

ctgtacgaga aagtgaagtc ccagctgaag aacaacgcca aagagatcgg caacggctgc   1440

ttcgagttct accacaagtg caacaacgag tgcatggaaa gcgtgaagaa cggaacctac   1500

gactacccca agtacagcga ggaaagcaag ctgaaccggg aagagatcga cggcgtgaag   1560

ctggaatcca tgggcgtgta ccagatcctg gccatctaca gcaccgtggc tagcagcctg   1620

gtgctgctgg tgtccctggg cgccatctcc ttttggatgt gctccaacgg cagcctgcag   1680

tgccggatct gcatc                                                    1695
```

```
<210> SEQ ID NO 10
<211> LENGTH: 565
<212> TYPE: PRT
<213> ORGANISM: Artificial Sequence
<220> FEATURE:
<223> OTHER INFORMATION: Influenza U2 amino acid sequence

<400> SEQUENCE: 10

Lys Ala Lys Leu Leu Val Leu Leu Cys Thr Phe Ala Ala Thr Asn Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Lys His Asn Gly Lys Leu Cys Lys Leu Lys Gly Ile Ala
    50                  55                  60

Pro Leu Gln Leu Gly Lys Cys Asn Ile Ala Gly Trp Ile Leu Gly Asn
65                  70                  75                  80

Pro Glu Cys Glu Ser Leu Ser Ser Lys Ser Ser Trp Ser Tyr Ile Val
                85                  90                  95

Glu Thr Pro Asn Ser Glu Asn Gly Thr Cys Tyr Pro Gly Asp Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Thr Ser Ser Trp Pro Asn His Asp Val
    130                 135                 140

Thr Lys Gly Val Thr Ala Ser Cys Ser His Ala Gly Ala Ser Ser Phe
145                 150                 155                 160

Tyr Lys Asn Leu Leu Trp Leu Thr Lys Lys Asn Gly Ser Tyr Pro Lys
                165                 170                 175

Leu Ser Lys Ser Tyr Ile Asn Asn Lys Glu Lys Glu Val Leu Val Leu
            180                 185                 190
```

-continued

```
Trp Gly Val His His Pro Ser Thr Ile Ala Asp Gln Gln Ser Leu Tyr
        195                 200                 205

Gln Asn Glu Asn Ala Tyr Val Ser Val Gly Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Ile Ser Asn Ala Pro Met
        275                 280                 285

His Asp Cys Asp Thr Lys Cys Gln Thr Pro Gln Gly Ala Ile Asn Ser
    290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 11
<211> LENGTH: 1809
<212> TYPE: DNA
<213> ORGANISM: Artificial Sequence
<220> FEATURE:
<223> OTHER INFORMATION: IgE-U2-HATAntigen DNA Sequence

<400> SEQUENCE: 11
ggtaccggat ccgccaccat ggactggacc tggattctgt tcctggtcgc cgctgctacc 60
cgggtgcact ctaaggccaa gctgctggtg ctgctgtgca ccttcgccgc caccaacgcc 120
gacaccatct gcatcggcta ccacgccaac aacagcaccg acaccgtgga taccgtgctg 180
gaaaagaacg tgaccgtgac ccacagcgtg aacctgctgg aagataagca caacggcaag 240
ctgtgcaagc tgaagggaat cgccccctg cagctgggca agtgcaatat cgccggctgg 300
attctgggca accccgagtg cgagagcctg agcagcaaga gcagctggtc ctacatcgtg 360
gaaaccccca acagcgagaa cggcacctgt taccccggcg acttcgccga ctacgaggaa 420
ctgcgcgagc agctgagcag cgtgtccagc ttcgagagat tcgagatctt ccccaagacc 480
agcagctggc ccaaccacga cgtgaccaag ggcgtgaccg ctagctgtag ccacgcaggc 540
gccagcagct tctacaagaa cctgctgtgg ctgaccaaga agaacggcag ctaccccaag 600
ctgagcaaga gctacatcaa caacaaagaa aaagaggtgc tggtcctctg ggcgtccac 660 caccccagca caatcgccga ccagcagagc ctgtaccaga acgagaacgc ctacgtgtcc 720
gtgggcagca gccactacag ccggaagttc acccccgaga tcgccaagcg gcccaaagtg 780
cgggaccagg aaggccggat caactactac tggaccctgc tggaacccgg cgacaccatc 840
atcttcgagg ccaacggcaa cctgatcgcc cccagatacg ccttcgccct gagcagaggc 900
ttcggcagcg gcatcatcat cagcaacgcc cccatgcacg actgcgacac caagtgccag 960
acccctcagg gcgccatcaa cagcagcctg cccttccaga acatccaccc cgtgaccatc 1020
ggcgagtgcc ccaaatacgt gcggagcacc aagctgcgga tggccaccgg cctgcggaac 1080
atccccagca tccagagcag aggcctgttc ggcgccattg ccggcttcat cgagggcggc 1140
tggaccggaa tggtggacgg gtggtacggc taccaccacc agaatgagca gggcagcggc 1200
tacgccgccg accagaagtc cacccagaac gccatcgacg gcatcaccaa caaagtgaac 1260
agcgtgatcg agaagatgaa cacccagttc accgccgtgg gcaaagagtt caacaagctg 1320
gaaaagcgga tggaaaacct gaacaagaag gtggacgacg gcttcctgga catctggacc 1380
tacaacgccg aactgctcgt gctgctggaa aacgagcgga ccctggactt ccacgacagc 1440
aacgtgaaga acctgtacga gaaagtgaag tcccagctga agaacaacgc caaagagatc 1500
ggcaacggct gcttcgagtt ctaccacaag tgcaacaacg agtgcatgga aagcgtgaag 1560
aacggaacct acgactaccc caagtacagc gaggaaagca agctgaaccg ggaagagatc 1620
gacggcgtga agctggaatc catgggcgtg taccagatcc tggccatcta cagcaccgtg 1680
gctagcagcc tggtgctgct ggtgtccctg ggcgccatct ccttttggat gtgctccaac 1740
ggcagcctgc agtgccggat ctgcatctac ccctacgacg tgcccgacta cgcctgatga 1800
ctcgagctc 1809

<210> SEQ ID NO 12
<211> LENGTH: 592
<212> TYPE: PRT
<213> ORGANISM: Artificial Sequence
<220> FEATURE:
<223> OTHER INFORMATION: IgE-U2-HATantigen amino acid Sequence

<400> SEQUENCE: 12

Met Asp Trp Thr Trp Ile Leu Phe Leu Val Ala Ala Ala Thr Arg Val
1 5 10 15

His Ser Lys Ala Lys Leu Leu Val Leu Leu Cys Thr Phe Ala Ala Thr

-continued

```
            20                  25                  30

Asn Ala Asp Thr Ile Cys Ile Gly Tyr His Ala Asn Asn Ser Thr Asp
        35                  40                  45

Thr Val Asp Thr Val Leu Glu Lys Asn Val Thr Val Thr His Ser Val
    50                  55                  60

Asn Leu Leu Glu Asp Lys His Asn Gly Lys Leu Cys Lys Leu Lys Gly
65                  70                  75                  80

Ile Ala Pro Leu Gln Leu Gly Lys Cys Asn Ile Ala Gly Trp Ile Leu
                85                  90                  95

Gly Asn Pro Glu Cys Glu Ser Leu Ser Ser Lys Ser Ser Trp Ser Tyr
            100                 105                 110

Ile Val Glu Thr Pro Asn Ser Glu Asn Gly Thr Cys Tyr Pro Gly Asp
        115                 120                 125

Phe Ala Asp Tyr Glu Glu Leu Arg Glu Gln Leu Ser Ser Val Ser Ser
    130                 135                 140

Phe Glu Arg Phe Glu Ile Phe Pro Lys Thr Ser Ser Trp Pro Asn His
145                 150                 155                 160

Asp Val Thr Lys Gly Val Thr Ala Ser Cys Ser His Ala Gly Ala Ser
                165                 170                 175

Ser Phe Tyr Lys Asn Leu Leu Trp Leu Thr Lys Lys Asn Gly Ser Tyr
            180                 185                 190

Pro Lys Leu Ser Lys Ser Tyr Ile Asn Asn Lys Glu Lys Glu Val Leu
        195                 200                 205

Val Leu Trp Gly Val His His Pro Ser Thr Ile Ala Asp Gln Gln Ser
    210                 215                 220

Leu Tyr Gln Asn Glu Asn Ala Tyr Val Ser Val Gly Ser Ser His Tyr
225                 230                 235                 240

Ser Arg Lys Phe Thr Pro Glu Ile Ala Lys Arg Pro Lys Val Arg Asp
                245                 250                 255

Gln Glu Gly Arg Ile Asn Tyr Tyr Trp Thr Leu Leu Glu Pro Gly Asp
            260                 265                 270

Thr Ile Ile Phe Glu Ala Asn Gly Asn Leu Ile Ala Pro Arg Tyr Ala
        275                 280                 285

Phe Ala Leu Ser Arg Gly Phe Gly Ser Gly Ile Ile Ile Ser Asn Ala
    290                 295                 300

Pro Met His Asp Cys Asp Thr Lys Cys Gln Thr Pro Gln Gly Ala Ile
305                 310                 315                 320

Asn Ser Ser Leu Pro Phe Gln Asn Ile His Pro Val Thr Ile Gly Glu
                325                 330                 335

Cys Pro Lys Tyr Val Arg Ser Thr Lys Leu Arg Met Ala Thr Gly Leu
            340                 345                 350

Arg Asn Ile Pro Ser Ile Gln Ser Arg Gly Leu Phe Gly Ala Ile Ala
        355                 360                 365

Gly Phe Ile Glu Gly Gly Trp Thr Gly Met Val Asp Gly Trp Tyr Gly
    370                 375                 380

Tyr His His Gln Asn Glu Gln Gly Ser Gly Tyr Ala Ala Asp Gln Lys
385                 390                 395                 400

Ser Thr Gln Asn Ala Ile Asp Gly Ile Thr Asn Lys Val Asn Ser Val
                405                 410                 415

Ile Glu Lys Met Asn Thr Gln Phe Thr Ala Val Gly Lys Glu Phe Asn
            420                 425                 430

Lys Leu Glu Lys Arg Met Glu Asn Leu Asn Lys Lys Val Asp Asp Gly
        435                 440                 445
```

-continued

```
Phe Leu Asp Ile Trp Thr Tyr Asn Ala Glu Leu Leu Val Leu Leu Glu
    450                 455                 460

Asn Glu Arg Thr Leu Asp Phe His Asp Ser Asn Val Lys Asn Leu Tyr
465                 470                 475                 480

Glu Lys Val Lys Ser Gln Leu Lys Asn Asn Ala Lys Glu Ile Gly Asn
                485                 490                 495

Gly Cys Phe Glu Phe Tyr His Lys Cys Asn Asn Glu Cys Met Glu Ser
            500                 505                 510

Val Lys Asn Gly Thr Tyr Asp Tyr Pro Lys Tyr Ser Glu Glu Ser Lys
        515                 520                 525

Leu Asn Arg Glu Glu Ile Asp Gly Val Lys Leu Glu Ser Met Gly Val
    530                 535                 540

Tyr Gln Ile Leu Ala Ile Tyr Ser Thr Val Ala Ser Ser Leu Val Leu
545                 550                 555                 560

Leu Val Ser Leu Gly Ala Ile Ser Phe Trp Met Cys Ser Asn Gly Ser
                565                 570                 575

Leu Gln Cys Arg Ile Cys Ile Tyr Pro Tyr Asp Val Pro Asp Tyr Ala
            580                 585                 590


<210> SEQ ID NO 13
<211> LENGTH: 1749
<212> TYPE: DNA
<213> ORGANISM: Artificial Sequence
<220> FEATURE:
<223> OTHER INFORMATION: BHA DNA Sequence

<400> SEQUENCE: 13

aaggccatca tcgtgctgct gatggtggtc acaagcaacg ccgaccggat ctgcaccggc     60

atcaccagca gcaacagccc ccacgtggtc aaaaccgcca cccagggcga agtgaacgtg    120

accggcgtga tcccccctgac caccaccccc accaagagcc acttcgccaa cctgaagggc    180

accaagaccc ggggaaagct gtgccccaag tgcctgaact gcaccgacct ggacgtggcc    240

ctgggcagac ctatgtgcgt gggcaccacc cctagcgcca aggccagcat cctgcacgaa    300

gtgcggcccg tgaccagcgg ctgcttcccc atcatgcacg accggaccaa gatccggcag    360

ctccccaacc tgctgcgggg ctacgagaac atccggctga gcacccagaa cgtgatcaac    420

gccgagaagg cccctggcgg cccttacaga ctgggcacaa gcggctcttg ccccaacgcc    480

accagcaaga gcggcttttt cgccacaatg gcctgggccg tgcccaagga caacaacaag    540

accgccacca accccctgac cgtggaagtg ccctacatct gcaccgaggg cgaggaccag    600

atcaccgtgt ggggcttcca cagcgataac aagacccaga tgaagaacct gtacggcgac    660

agcaaccccc agaagttcac cagctccgcc aacggcgtga ccacccacta cgtgtcccag    720

atcggcggct tccccgacca gacagaggat ggcggcctgc cccagagcgg cagaatcgtg    780

gtggactaca tggtgcagaa gcccggcaag accggcacca tcgtgtacca gcggggcatc    840

ctgctgcccc agaaagtgtg gtgcgccagc ggccggtcca aagtgatcaa gggcagcctg    900

cctctgatcg gcgaggccga ttgcctgcac gagaagtacg gcggcctgaa caagagcaag    960

ccctactaca ccggcgagca cgccaaagcc atcggcaact gccccatctg ggtcaaaacc   1020

cccctgaagc tggccaacgg caccaagtac cggcctcccg ccaagctgct gaaagagcgg   1080

ggcttcttcg gcgctatcgc cggctttctg gaaggcggct gggagggcat gatcgccggc   1140

tggcacggct acacatctca cggcgctcat ggcgtggccg tggccgctga tctgaagtcc   1200

acccaggaag ccatcaacaa gatcaccaag aacctgaaca gcctgagcga gctggaagtg   1260
```

aagaatctgc agcggctgag cggcgccatg gacgagctgc acaacgagat cctggaactg 1320
gacgagaagg tggacgacct gcgggccgac accatctcca gccagatcga gctggccgtg 1380
ctgctgtcca acgagggcat catcaacagc gaggacgagc atctgctggc cctggaacgg 1440
aagctgaaga agatgctggg ccctagcgcc gtggacatcg gcaacggctg cttcgagaca 1500
aagcacaagt gcaaccagac ctgcctggac cggatcgctg ccggcacctt caacgccggc 1560
gagttcagcc tgcccacctt cgacagcctg aacatcaccg ccgccagcct gaacgacgac 1620
ggcctggaca accacaccat cctgctgtac tacagcaccg cagcctccag cctggccgtg 1680
accctgatga tcgccatctt catcgtgtac atggtgtctc gggacaacgt gtcctgcagc 1740
atctgcctg 1749

<210> SEQ ID NO 14
<211> LENGTH: 583
<212> TYPE: PRT
<213> ORGANISM: Artificial Sequence
<220> FEATURE:
<223> OTHER INFORMATION: BHA Amino Acid Sequence

<400> SEQUENCE: 14

Lys Ala Ile Ile Val Leu Leu Met Val Val Thr Ser Asn Ala Asp Arg
1 5 10 15

Ile Cys Thr Gly Ile Thr Ser Ser Asn Ser Pro His Val Val Lys Thr
20 25 30

Ala Thr Gln Gly Glu Val Asn Val Thr Gly Val Ile Pro Leu Thr Thr
35 40 45

Thr Pro Thr Lys Ser His Phe Ala Asn Leu Lys Gly Thr Lys Thr Arg
50 55 60

Gly Lys Leu Cys Pro Lys Cys Leu Asn Cys Thr Asp Leu Asp Val Ala
65 70 75 80

Leu Gly Arg Pro Met Cys Val Gly Thr Thr Pro Ser Ala Lys Ala Ser
85 90 95

Ile Leu His Glu Val Arg Pro Val Thr Ser Gly Cys Phe Pro Ile Met
100 105 110

His Asp Arg Thr Lys Ile Arg Gln Leu Pro Asn Leu Leu Arg Gly Tyr
115 120 125

Glu Asn Ile Arg Leu Ser Thr Gln Asn Val Ile Asn Ala Glu Lys Ala
130 135 140

Pro Gly Gly Pro Tyr Arg Leu Gly Thr Ser Gly Ser Cys Pro Asn Ala
145 150 155 160

Thr Ser Lys Ser Gly Phe Phe Ala Thr Met Ala Trp Ala Val Pro Lys
165 170 175

Asp Asn Asn Lys Thr Ala Thr Asn Pro Leu Thr Val Glu Val Pro Tyr
180 185 190

Ile Cys Thr Glu Gly Glu Asp Gln Ile Thr Val Trp Gly Phe His Ser
195 200 205

Asp Asn Lys Thr Gln Met Lys Asn Leu Tyr Gly Asp Ser Asn Pro Gln
210 215 220

Lys Phe Thr Ser Ser Ala Asn Gly Val Thr Thr His Tyr Val Ser Gln
225 230 235 240

Ile Gly Gly Phe Pro Asp Gln Thr Glu Asp Gly Gly Leu Pro Gln Ser
245 250 255

Gly Arg Ile Val Val Asp Tyr Met Val Gln Lys Pro Gly Lys Thr Gly
260 265 270

-continued

```
Thr Ile Val Tyr Gln Arg Gly Ile Leu Leu Pro Gln Lys Val Trp Cys
        275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
        355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580
```

<210> SEQ ID NO 15
<211> LENGTH: 1865
<212> TYPE: DNA
<213> ORGANISM: Artificial Sequence
<220> FEATURE:
<223> OTHER INFORMATION: IgE-BHA-HATantigen DNA Sequence

<400> SEQUENCE: 15

```
ggtaccggat ccgccaccat ggactggacc tggattctgt tcctggtggc cgctgccaca      60

cgggtgcaca gcaaggccat catcgtgctg ctgatggtgg tcacaagcaa cgccgaccgg     120

atctgcaccg gcatcaccag cagcaacagc ccccacgtgg tcaaaaccgc cacccagggc     180

gaagtgaacg tgaccggcgt gatccccctg accaccaccc ccaccaagag ccacttcgcc     240
```

-continued

```
aacctgaagg gcaccaagac ccggggaaag ctgtgcccca agtgcctgaa ctgcaccgac    300

ctggacgtgg ccctgggcag acctatgtgc gtgggcacca cccctagcgc caaggccagc    360

atcctgcacg aagtgcggcc cgtgaccagc ggctgcttcc ccatcatgca cgaccggacc    420

aagatccggc agctccccaa cctgctgcgg ggctacgaga acatccggct gagcacccag    480

aacgtgatca acgccgagaa ggcccctggc ggcccttaca gactgggcac aagcggctct    540

tgccccaacg ccaccagcaa gagcggcttt ttcgccacaa tggcctgggc cgtgcccaag    600

gacaacaaca agaccgccac caacccccctg accgtggaag tgccctacat ctgcaccgag    660

ggcgaggacc agatcaccgt gtggggcttc cacagcgata acaagaccca gatgaagaac    720

ctgtacggcg acagcaaccc ccagaagttc accagctccg ccaacggcgt gaccacccac    780

tacgtgtccc agatcggcgg cttccccgac cagacagagg atggcggcct gccccagagc    840

ggcagaatcg tggtggacta catggtgcag aagcccggca agaccggcac catcgtgtac    900

cagcggggca tcctgctgcc ccagaaagtg tggtgcgcca gcggccggtc caaagtgatc    960

aagggcagcc tgcctctgat cggcgaggcc gattgcctgc acgagaagta cggcggcctg   1020

aacaagagca agccctacta caccggcgag cacgccaaag ccatcggcaa ctgccccatc   1080

tgggtcaaaa ccccccctgaa gctggccaac ggcaccaagt accggcctcc cgccaagctg   1140

ctgaaagagc ggggcttctt cggcgctatc gccggctttc tggaaggcgg ctgggagggc   1200

atgatcgccg gctggcacgg ctacacatct cacggcgctc atggcgtggc cgtggccgct   1260

gatctgaagt ccacccagga agccatcaac aagatcacca agaacctgaa cagcctgagc   1320

gagctggaag tgaagaatct gcagcggctg agcggcgcca tggacgagct gcacaacgag   1380

atcctggaac tggacgagaa ggtggacgac ctgcgggccg acaccatctc cagccagatc   1440

gagctggccg tgctgctgtc caacgagggc atcatcaaca gcgaggacga gcatctgctg   1500

gccctggaac ggaagctgaa gaagatgctg ggccctagcg ccgtggacat cggcaacggc   1560

tgcttcgaga caaagcacaa gtgcaaccag acctgcctgg accggatcgc tgccggcacc   1620

ttcaacgccg gcgagttcag cctgcccacc ttcgacagcc tgaacatcac cgccgccagc   1680

ctgaacgacg acggcctgga caaccacacc atcctgctgt actacagcac cgcagcctcc   1740

agcctggccg tgaccctgat gatcgccatc ttcatcgtgt acatggtgtc tcgggacaac   1800

gtgtcctgca gcatctgcct gtacccctac gacgtgcccg actacgctga tgactcgagc   1860

tcctc                                                                1865
```

```
<210> SEQ ID NO 16
<211> LENGTH: 610
<212> TYPE: PRT
<213> ORGANISM: Artificial Sequence
<220> FEATURE:
<223> OTHER INFORMATION: IgE-BHA-HATantigen Amino Acid Sequence

<400> SEQUENCE: 16

Met Asp Trp Thr Trp Ile Leu Phe Leu Val Ala Ala Ala Thr Arg Val
1               5                   10                  15

His Ser Lys Ala Ile Ile Val Leu Leu Met Val Val Thr Ser Asn Ala
            20                  25                  30

Asp Arg Ile Cys Thr Gly Ile Thr Ser Ser Asn Ser Pro His Val Val
        35                  40                  45

Lys Thr Ala Thr Gln Gly Glu Val Asn Val Thr Gly Val Ile Pro Leu
    50                  55                  60

Thr Thr Thr Pro Thr Lys Ser His Phe Ala Asn Leu Lys Gly Thr Lys
```

-continued

```
65                  70                  75                  80

Thr Arg Gly Lys Leu Cys Pro Lys Cys Leu Asn Cys Thr Asp Leu Asp
                85                  90                  95

Val Ala Leu Gly Arg Pro Met Cys Val Gly Thr Thr Pro Ser Ala Lys
            100                 105                 110

Ala Ser Ile Leu His Glu Val Arg Pro Val Thr Ser Gly Cys Phe Pro
        115                 120                 125

Ile Met His Asp Arg Thr Lys Ile Arg Gln Leu Pro Asn Leu Leu Arg
    130                 135                 140

Gly Tyr Glu Asn Ile Arg Leu Ser Thr Gln Asn Val Ile Asn Ala Glu
145                 150                 155                 160

Lys Ala Pro Gly Gly Pro Tyr Arg Leu Gly Thr Ser Gly Ser Cys Pro
                165                 170                 175

Asn Ala Thr Ser Lys Ser Gly Phe Phe Ala Thr Met Ala Trp Ala Val
            180                 185                 190

Pro Lys Asp Asn Asn Lys Thr Ala Thr Asn Pro Leu Thr Val Glu Val
        195                 200                 205

Pro Tyr Ile Cys Thr Glu Gly Glu Asp Gln Ile Thr Val Trp Gly Phe
    210                 215                 220

His Ser Asp Asn Lys Thr Gln Met Lys Asn Leu Tyr Gly Asp Ser Asn
225                 230                 235                 240

Pro Gln Lys Phe Thr Ser Ser Ala Asn Gly Val Thr Thr His Tyr Val
                245                 250                 255

Ser Gln Ile Gly Gly Phe Pro Asp Gln Thr Glu Asp Gly Gly Leu Pro
            260                 265                 270

Gln Ser Gly Arg Ile Val Val Asp Tyr Met Val Gln Lys Pro Gly Lys
        275                 280                 285

Thr Gly Thr Ile Val Tyr Gln Arg Gly Ile Leu Leu Pro Gln Lys Val
    290                 295                 300

Trp Cys Ala Ser Gly Arg Ser Lys Val Ile Lys Gly Ser Leu Pro Leu
305                 310                 315                 320

Ile Gly Glu Ala Asp Cys Leu His Glu Lys Tyr Gly Gly Leu Asn Lys
                325                 330                 335

Ser Lys Pro Tyr Tyr Thr Gly Glu His Ala Lys Ala Ile Gly Asn Cys
            340                 345                 350

Pro Ile Trp Val Lys Thr Pro Leu Lys Leu Ala Asn Gly Thr Lys Tyr
        355                 360                 365

Arg Pro Pro Ala Lys Leu Leu Lys Glu Arg Gly Phe Phe Gly Ala Ile
    370                 375                 380

Ala Gly Phe Leu Glu Gly Gly Trp Glu Gly Met Ile Ala Gly Trp His
385                 390                 395                 400

Gly Tyr Thr Ser His Gly Ala His Gly Val Ala Val Ala Ala Asp Leu
                405                 410                 415

Lys Ser Thr Gln Glu Ala Ile Asn Lys Ile Thr Lys Asn Leu Asn Ser
            420                 425                 430

Leu Ser Glu Leu Glu Val Lys Asn Leu Gln Arg Leu Ser Gly Ala Met
        435                 440                 445

Asp Glu Leu His Asn Glu Ile Leu Glu Leu Asp Glu Lys Val Asp Asp
    450                 455                 460

Leu Arg Ala Asp Thr Ile Ser Ser Gln Ile Glu Leu Ala Val Leu Leu
465                 470                 475                 480

Ser Asn Glu Gly Ile Ile Asn Ser Glu Asp Glu His Leu Leu Ala Leu
                485                 490                 495
```

```
Glu Arg Lys Leu Lys Lys Met Leu Gly Pro Ser Ala Val Asp Ile Gly
            500                 505                 510

Asn Gly Cys Phe Glu Thr Lys His Lys Cys Asn Gln Thr Cys Leu Asp
        515                 520                 525

Arg Ile Ala Ala Gly Thr Phe Asn Ala Gly Glu Phe Ser Leu Pro Thr
    530                 535                 540

Phe Asp Ser Leu Asn Ile Thr Ala Ala Ser Leu Asn Asp Asp Gly Leu
545                 550                 555                 560

Asp Asn His Thr Ile Leu Leu Tyr Tyr Ser Thr Ala Ala Ser Ser Leu
                565                 570                 575

Ala Val Thr Leu Met Ile Ala Ile Phe Ile Val Tyr Met Val Ser Arg
            580                 585                 590

Asp Asn Val Ser Cys Ser Ile Cys Leu Tyr Pro Tyr Asp Val Pro Asp
        595                 600                 605

Tyr Ala
    610


<210> SEQ ID NO 17
<211> LENGTH: 18
<212> TYPE: PRT
<213> ORGANISM: Artificial Sequence
<220> FEATURE:
<223> OTHER INFORMATION: IgE Leader Amino Acid Sequence

<400> SEQUENCE: 17

Met Asp Trp Thr Trp Ile Leu Phe Leu Val Ala Ala Ala Thr Arg Val
1               5                   10                  15

His Ser


<210> SEQ ID NO 18
<211> LENGTH: 9
<212> TYPE: PRT
<213> ORGANISM: Artificial Sequence
<220> FEATURE:
<223> OTHER INFORMATION: HA tag amino acid sequence

<400> SEQUENCE: 18

Tyr Pro Tyr Asp Val Pro Asp Tyr Ala
1               5


<210> SEQ ID NO 19
<211> LENGTH: 1728
<212> TYPE: DNA
<213> ORGANISM: Artificial Sequence
<220> FEATURE:
<223> OTHER INFORMATION: Influenza H1 consensu sequence

<400> SEQUENCE: 19

ggtaccaagc ttgccaccat gaaggtgaaa ctgctggtgc tgctgtgcac cttcaccgcc      60

acctacgccg acaccatctg catcggctac cacgccaaca acagcaccga caccgtggat     120

accgtgctgg aaaagaacgt gaccgtgacc cacagcgtga acctgctgga agatagccac     180

aacggcaagc tgtgcctgct gaaaggcatc gcccccctgc agctgggcaa ctgcagcgtg     240

gccggctgga tcctgggcaa ccccgagtgc gagctgctga tttccaaaga aagctggtcc     300

tacatcgtgg agacccccaa ccccgagaac ggcacctgct accccggcta cttcgccgac     360

tacgaggaac tgcgggagca gctgtccagc gtgagcagct tcgagcggtt cgagatcttc     420

cccaaagaga gcagctggcc caaccacacc gtgaccggcg tgagcgccag ctgctcccac     480
```

aatggcaaga gcagcttcta ccggaacctg ctgtggctga ccggcaagaa cggcctgtac 540
cccaacctga gcaagagcta cgccaataac aaagaaaagg aagtgctggt gctgtggggc 600
gtgcaccacc cccccaacat cggcgaccag cgggccctgt accacaccga gaacgcctac 660
gtgagcgtgg tgtccagcca ctacagccgg cggttcaccc ccgagatcgc caagcggccc 720
aaagtgcggg accaggaagg ccggatcaac tactactgga ccctgctgga acccggcgac 780
accatcatct tcgaggccaa cggcaacctg atcgcccccca gatacgcctt cgccctgagc 840
cggggcttcg gcagcggcat catcaccagc aacgccccca tggacgagtg cgacgccaag 900
tgccagaccc ctcagggagc tattaacagc agcctgccct tccagaacgt gcaccccgtg 960
accatcggcg agtgccccaa gtacgtgcgg agcgccaagc tgcggatggt gaccggcctg 1020
cggaacatcc ccagcatcca gagcaggggc ctgttcggcg ccatcgccgg cttcatcgag 1080
ggcggctgga ccggcatggt ggacgggtgg tacggctacc accaccagaa cgagcagggc 1140
agcggctacg ccgccgacca gaagagcacc cagaacgcca tcaacggcat caccaacaag 1200
gtgaacagcg tgatcgagaa gatgaacacc cagttcaccg ccgtgggcaa agagttcaac 1260
aagctggaac ggcggatgga aaacctgaac aagaaggtgg acgacggctt cctggacatc 1320
tggacctaca acgccgagct gctggtgctg ctggaaaacg agcggaccct ggacttccac 1380
gacagcaacg tgaagaacct gtacgagaag gtgaaaagcc agctgaagaa caacgccaaa 1440
gagatcggca acggctgctt cgagttctac cacaagtgca acgacgagtg catggaaagc 1500
gtgaagaatg gcacctacga ctaccccaag tacagcgagg aaagcaagct gaaccgggag 1560
aagatcgacg gcgtgaagct ggaaagcatg ggcgtgtacc agatcctggc catctacagc 1620
accgtcgctt ccagcctcgt cctgctcgtg tccctgggcg ccatctcctt ttggatgtgc 1680
agcaacggca gcctgcagtg ccggatctgc atctgatgac tcgagctc 1728

<210> SEQ ID NO 20
<211> LENGTH: 1731
<212> TYPE: DNA
<213> ORGANISM: Artificial Sequence
<220> FEATURE:
<223> OTHER INFORMATION: Influenza H3 consensus sequence

<400> SEQUENCE: 20
ggtaccaagc ttgccaccat gaaaaccatc atcgccctga gctacatcct gtgcctggtg 60
ttcgcccaga agctgcccgg caacgacaac agcaccgcca ccctgtgtct gggccaccac 120
gccgtgccca acggcaccat cgtgaaaaca atcaccaacg accagatcga ggtgaccaac 180
gccaccgagc tggtgcagag cagcagcacc ggcggcatct gcgacagccc ccaccagatc 240
ctggacggcg agaactgcac cctgatcgac gccctgctgg gcgaccctca gtgcgacggc 300
ttccagaaca aaaagtggga cctgttcgtg gagcggagca aggcctacag caactgctac 360
ccctacgacg tgcccgacta cgccagcctg cggagcctgg tggccagcag cggcaccctg 420
gaattcaaca acgagagctt caactggacc ggcgtgaccc agaacggcac cagcagcgcc 480
tgcaagcggc ggagcaacaa cagcttcttt tccagactga actggctgac ccacctgaag 540
ttcaagtacc ccgccctgaa cgtgaccatg cccaacaatg agaagttcga caagctgtac 600
atctggggcg tgcaccaccc cggcaccgac aatgaccaga tcagcctgta cgcccaggcc 660
agcggccgga tcaccgtgag caccaagcgg agccagcaga ccgtgatccc caacatcggc 720
agccggccca gagtgagaga catccccagc cggatcagca tctactggac aatcgtgaag 780
cccggcgaca tcctgctgat caactccacc ggcaacctga tcgcccccag gggctacttc 840

-continued

```
aagatcagaa gcggcaagag cagcatcatg cggagcgacg cccccatcgg caagtgcaac    900
agcgagtgca tcaccccaa tggcagcatc cccaacgaca agcccttcca gaacgtgaac     960
cggatcacct acggcgcctg ccccagatac gtgaagcaga acaccctgaa gctggccacc   1020
ggcatgcgga acgtgcccga gaagcagacc cggggcatct tcggcgccat cgccggcttc   1080
atcgagaacg gctgggaggg catggtggac gggtggtacg gcttccggca ccagaactcc   1140
gagggcatcg gccaggccgc cgacctgaag agcacccagg ccgccatcaa ccagatcaac   1200
ggcaagctga accggctgat cggcaagacc aacgagaagt tccaccagat cgaaaaagaa   1260
ttcagcgagg tggagggccg gatccaggac ctggaaaagt acgtggagga caccaagatc   1320
gacctgtgga gctacaacgc cgagctgctg gtcgccctgg aaaaccagca caccatcgac   1380
ctgaccgaca gcgagatgaa caagctgttc gagcggacca agaagcagct gcgggagaac   1440
gccgaggaca tgggcaacgg ctgctttaag atctaccaca agtgcgacaa cgcctgcatc   1500
ggcagcatcc ggaacggcac ctacgaccac gacgtgtacc gggacgaggc cctgaacaac   1560
cggttccaga tcaagggcgt ggagctgaag agcggctaca aggactggat cctgtggatc   1620
agcttcgcca tcagctgctt tctgctgtgc gtggccctgc tgggattcat catgtgggcc   1680
tgccagaagg gcaacatccg ctgcaacatc tgcatctgat gactcgagct c            1731
```